United States Patent
Safo et al.

(10) Patent No.: US 12,065,408 B2
(45) Date of Patent: Aug. 20, 2024

(54) BENZALDEHYDE COMPOUNDS WITH DIRECT POLYMER DESTABILIZING EFFECTS TO TREAT SICKLE CELL DISEASE

(71) Applicants: VIRGINIA COMMONWEALTH UNIVERSITY, Richmond, VA (US); IIIExcor Holdings, LLC, Henrico, VA (US); KING ABDULAZIZ UNIVERSITY, Jeddah (SA); CHILDREN'S HOSPITAL OF PHILADELPHIA (CHOP), Philadelphia, PA (US)

(72) Inventors: Martin Safo, Richmond, VA (US); Yan Zhang, Glen Allen, VA (US); Andrew Fleischman, Henrico, VA (US); David Light, Henrico, VA (US); Moustafa El-Araby, Jeddah (SA); Abdelsattar Omar, Jeddah (SA); Osheiza Abdulmalik, Philadelphia, PA (US)

(73) Assignees: VIRGINIA COMMONWEALTH UNIVERISTY, Richmond, VA (US); KING ABDULAZIZ UNIVERSITY, Jeddah (SA); CHILDREN'S HOSPITAL OF PHILADELPHIA (CHOP), Philadelphia, PA (US); ILLEXCOR HOLDINGS, LLC, Henrico, VA (US)

(*) Notice: Subject to any disclaimer, the term of this patent is extended or adjusted under 35 U.S.C. 154(b) by 0 days.

(21) Appl. No.: 18/386,724

(22) Filed: Nov. 3, 2023

(65) Prior Publication Data

US 2024/0174612 A1 May 30, 2024

Related U.S. Application Data

(60) Provisional application No. 63/423,167, filed on Nov. 7, 2022, provisional application No. 63/442,824, filed on Feb. 2, 2023.

(51) Int. Cl.
*C07D 213/30* (2006.01)
*A61P 7/06* (2006.01)
*C07D 239/26* (2006.01)

(52) U.S. Cl.
CPC .............. *C07D 213/30* (2013.01); *A61P 7/06* (2018.01); *C07D 239/26* (2013.01)

(58) Field of Classification Search
CPC ........ C07D 239/26; C07D 213/30; A61P 7/06
See application file for complete search history.

(56) References Cited

PUBLICATIONS

Abdulmalik, O., Pagare, P.P., Huang, B et al. VZHE-039, a novel antisickling agent that prevents erythrocyte sickling under both hypoxic and anoxic conditions. Sci Rep 10, 20277 (2020). https://doi.org/10.1038/s41598-020-77171-2.*

* cited by examiner

*Primary Examiner* — Rebecca L Anderson
(74) *Attorney, Agent, or Firm* — WC&F IP

(57) ABSTRACT

Compounds and methods for preventing and/or treating one or more symptoms of sickle cell diseases (SCD) by administering at least one of the compounds are provided. The compounds are chemically modified to increase bioavailability and activity, e.g., so that the compounds prevent adhesion and sickling of red blood cells (RBCs).

11 Claims, 5 Drawing Sheets

BENZALDEHYDE COMPOUNDS WITH DIRECT POLYMER DESTABILIZING EFFECTS TO TREAT SICKLE CELL DISEASE

CROSS-REFERENCE TO RELATED APPLICATIONS

This application claims priority to U.S. Ser. No. 63/423,167 filed Nov. 7, 2022, and to U.S. Ser. No. 63/442,824 filed Feb. 2, 2023, and the complete contents of these is herein incorporated by reference.

STATEMENT OF FEDERALLY SPONSORED RESEARCH AND DEVELOPMENT

This invention was made with government support under contract numbers HL156158, HL154864, and MD009124 awarded by the National Institutes of Health. The United States government has certain rights in the invention.

BACKGROUND OF THE INVENTION

Field of the Invention

The invention generally relates to compounds that exhibit enhanced activity and safety for the treatment of sickle cell disease (SCD). In particular, the compounds are aromatic aldehydes that exhibit highly potent polymer destabilizing effects.

Description of Related Art

Hemoglobin (Hb) functions to carry oxygen through the blood and release it to tissues by equilibrating between two allosteric states: a tense (T) state, which exhibits low-affinity for oxygen, and a relaxed (R) state, which exhibits high affinity for oxygen. Sickle cell disease (SCD) is an inherited hematologic disorder and occurs as a result of replacement of βGlu6 with βVal6 in Hb, forming sickle Hb (HbS). Under hypoxia or low oxygen ($O_2$) tension, which leads to an increased concentration of the low-affinity deoxygenated (T-state) Hb, HbS polymerizes into long, rigid, and insoluble fibers resulting in sickling of red blood cells (RBCs). The polymer which is initiated by the primary interaction involving βVal6 is stabilized by several other secondary contacts between the HbS molecules. Hypoxia-induced sickling leads to secondary pathophysiological effects, e.g. adhesion of RBCs to tissue endothelium, oxidative stress/damage, hemolysis (rupture) of RBCs, inflammation, vaso-occlusion, impaired microvascular blood flow, and decreased vascular nitric oxide bioavailability, which eventually lead to severe morbidity, such as painful crises, stroke, kidney failure, pulmonary hypertension, and premature mortality. Prior to the recent FDA approval of Voxclotor (Oxbryta), the only oral drugs approved for treating SCD were hydroxyurea (HU) and L-glutamine (Endari™). HU induces γ-globin expression to form fetal Hb (HbF), which can directly inhibit HbS polymerization and RBC sickling. However, not all patients respond to HU and responses may be limited. HU can also cause myelosuppression, a life-threatening adverse effect. While L-glutamine may have anti-oxidant properties that can reduce the frequency of pain crises, efficacy is limited and the drug is seldom used. More effective oral drugs are urgently needed, especially in the face of the significant morbidity, mortality, healthcare disparities, and public health burden imposed by SCD.

Aromatic aldehydes, such as Voxelotor, bind to the α-cleft of Hb and shift the allosteric equilibrium to the high-affinity R-state of HbS, which does not polymerize. Allosteric modulators have a clinical benefit for patients with SCD. In the Phase III HOPE trial, Voxelotor reduced markers of hemolysis and improved anemia by increasing Hb concentrations by at least 1 g/dl in most patients. However, the disease-modifying clinical effects of Voxelotor were modest, with persistent signs of chronic inflammation and hemolysis. For example, a significant reduction in vaso-occlusive events was not observed. The major physiologic impact of allosteric modulation is HbS dilution; drug-bound oxygenated HbS tetramers cannot be incorporated into polymers and, thus, there are fewer Hb tetramers available to polymerize. However, the magnitude of clinical benefit from HbS dilution is limited, and patients on Voxelotor have significant residual disease sequalae that impacts quality of life and longevity. Furthermore, the on-target pharmacodynamic effects of the drug on Hb allosteric states are directly dose limiting, as further increases in Hb $O_2$-affinity would limit release of $O_2$ to tissues and, eventually, induce clinical signs of tissue hypoxia. Drugs that can directly inhibit HbS polymerization may have more disease-modifying benefits. For example, it is well known that individuals with a rare co-inherited condition in which HbF levels remain above 25% into adulthood have essentially no clinical disease. HbF interferes with important lateral contacts to directly destabilize polymerization. Similarly, individuals with a rare co-inherited Hb variant, Hb Stanleyville, also have a benign clinical phenotype with essentially no disease due to a lysine mutation on the surface of αF-helix of HbS that interrupts polymer stabilizing contacts.

A number of aromatic aldehydes that act directly on HbS to inhibit polymerization have been discovered to date. These compounds generally have comprised a benzaldehyde with a second ring structure (pyridine or benzene) connected to the benzaldehyde via a methoxy bridge ortho to the aldehyde group. The methoxy bridge positioned ortho to the aldehyde group on the benzaldehyde allows the second ring structure to extend towards the mouth of the α-cleft to make interactions with surface-located residues on the αF-helix of HbS. Compounds that make strong interactions with key αF-helix residues can destabilize HbS polymers by perturbing important secondary stabilizing contacts. Examples of a previously discovered compound is INN-310 (SAJ-310), which contains a methoxy meta to the aldehyde on the benzaldehyde ring and no substituents on a pyridine ring. INN-310 showed only very weak polymer destabilizing effects in vitro, likely due to limited interactions with αF-helix residues, and moreover, exhibited suboptimal pharmacokinetic properties in vivo. Further examples of highly potent polymer destabilizing compounds with improved pharmacokinetic properties include VZHE-039 and PP-14. Instead of a meta methoxy as with INN-310, VZHE-039 and PP-14 contain an ortho hydroxyl on the benzaldehyde that forms an intramolecular interaction that stabilizes and protects the aldehyde from rapid oxidative metabolism. Both VZHE-039 and PP-14 each also incorporate an additional chemical substituent on the second ring that can make strong hydrogen-bonding and hydrophobic interactions with the αF-helix; as anticipated, these interactions significantly improved the potency of polymer destabilizing effects. However, up to this point, the addition of chemical substituents on the second ring has also introduced significant drawbacks that have prevented any compound from becoming a viable human drug candidate. Substituents on the second ring have either proven to be metabolically labile (carboxylester or carboxylamide), introduced charged species (carboxylic acid) that may have reduced membrane permeability, or have been hepatotoxic (methyl hydroxyl). Hundreds of compounds containing different classes of chemical substituents added to the second ring to target the αF-helix have been tested to date. Nevertheless, no compounds had yet been discovered that are both highly potent polymer destabilizers and can safely and reliably achieve therapeutic drug levels required for the chronic oral treatment of SCD.

There is an urgent need to develop new non-toxic anti-sickling agents that have more potent and sustained polymer destabilizing effects, exhibit a long duration of pharmacologic action, and have acceptable oral bioavailability to be administered as an oral drug.

SUMMARY OF THE INVENTION

Other features and advantages of the present invention will be set forth in the description of invention that follows, and, in part, will be apparent from the description or may be learned by practice of the invention. The invention will be realized and attained by the compositions and methods particularly pointed out in the written description and claims hereof.

It is an object of the present disclosure to provide a compound having a formula

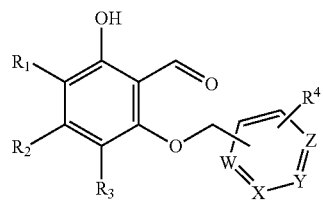

wherein W, X, Y and Z are the same or different and are independently C or N, with the proviso that at least one of W, X, Y, and Z is N, and $R_1$, $R_2$, $R_3$, and $R_4$ are the same or different and independently F, Cl or H, and pharmaceutically acceptable salts or prodrugs thereof.

In some aspects, the compound is

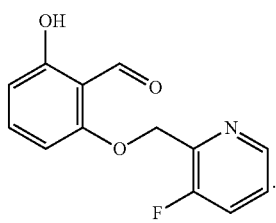 [SMILES: O=Cc1c(O)cccc1OCc1ncccc1F]

In other aspects, the compound is

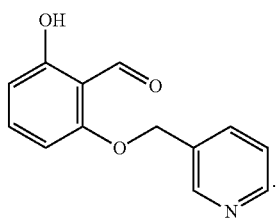 [SMILES: O=Cc1c(O)cccc1OCc1cccnc1]

In further aspects, the compound is

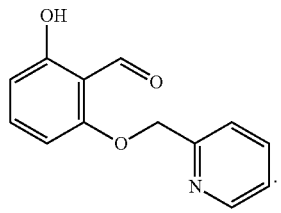 [SMILES: O=Cc1c(O)cccc1OCc1ccccn1]

In yet further aspects, at least one of $R_1$, $R_2$, $R_3$, and $R_4$ is independently F or Cl. In additional aspects, the compound is

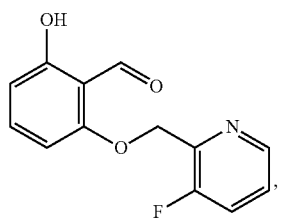

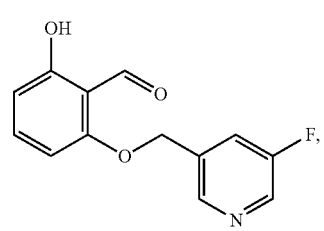

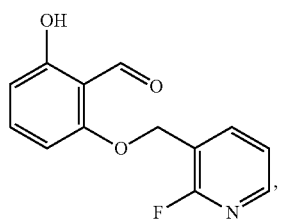

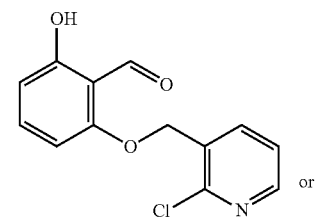

or

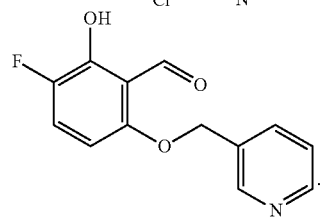

In alternative aspects, the compound is

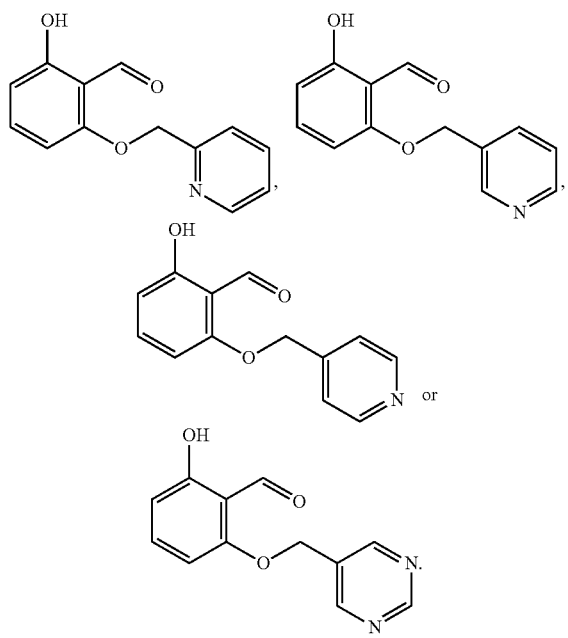

Also provided is a method of preventing or treating one or more symptoms or conditions of sickle cell disease (SCD) in a subject in need thereof, comprising administering to the subject a therapeutically effective amount of at least one compound having a formula

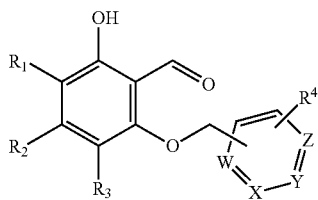

wherein W, X, Y and Z are the same or different and are independently C or N, with the proviso that at least one of W, X, Y and Z is N; and $R_1$, $R_2$, $R_3$, and $R_4$ are the same or different and independently F, Cl or H. In some aspects, the one or more symptoms or conditions are selected from the group consisting of red blood cell (RBC) sickling, adhesion of RBCs to tissue endothelium, oxidative stress and/or damage, hemolysis of RBCs, inflammation, vaso-occlusion, impaired microvascular blood flow, stroke, pain, and death. In further aspects, the step of administering is performed orally.

DETAILED DESCRIPTION

Figure 1:
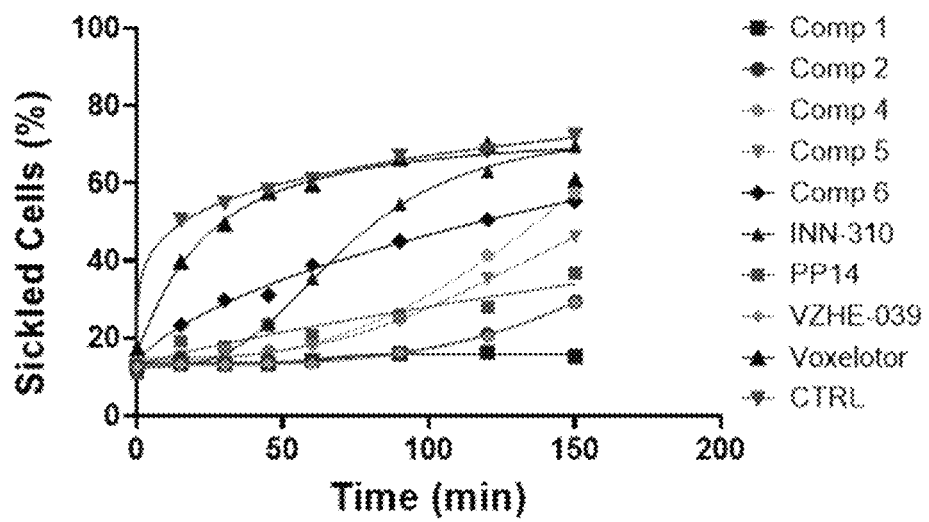
FIG. 1. Time-dependent sickling under anoxia.

Disclosed herein are benzaldehyde compounds that, unexpectedly, demonstrate potent and sustained polymer destabilization, in addition to allosteric modulation to increase the affinity of HbS for oxygen, despite having no chemical substituent on the second ring (pyridine or benzene) to make direct interactions with the αF-helix residues of HbS. These compounds lack a carboxylester, carboxylamide, methyl hydroxyl, or similar pharmacophore on the second ring that can make hydrogen bond interactions with surface residues of the αF-helix. However, unexpectedly, these compounds make very strong interactions with the a F-helix residues that are either entirely water-mediated directly through a pyridine, or alternatively a pyrimidine or triazine nitrogen, or even entirely hydrophobic via a benzene ring. Even more surprisingly, the direct polymer destabilization effects of some compounds in this group are the most potent observed to date, with sustained inhibition of RBC sickling in vitro for greater than 150 minutes. The results are unexpected because previously discovered compounds, e.g. INN-310, with no additional chemical substituents on the second ring to interact with the αF-helix demonstrated only very weak polymer destabilization effects, which was presumed to be due to lack of hydrogen-bond interactions. Thus, it was surprising that compounds in the present invention were not only potent, but the most potent discovered to date. The unexpected result appears to be the consequence of changes in the orientation of the compounds in the Hb a cleft with the addition of the ortho hydroxyl on the benzaldehyde ring to replace the meta methoxy of INN-310. This, fortuitously, moved the second ring structure in position to make its own strong interactions with a F-helix residues without any chemical substituents required. This is supported by the fact that changing the ortho hydroxyl to a halogen completely eliminated the polymer destabilizing effects of the compound. In retrospect, this also explains the reduced in vitro potency of TD-7, an analogue of VZHE-039, with meta methoxy instead of ortho hydroxy on the benzaldehyde similar to INN-310. The surface residues of αF helix of HbS are important for stabilizing the polymers through secondary interactions with the adjacent HbS. It is well known and accepted that the HbS variant Stanleyville, with a co-inheritance mutation on the surface of the αF-helix (αAsn78↔aLsy78), has limited polymerization. Without being bound by theory, it is believed that the compounds of the present invention interact with the surface located αF helix of HbS, and this interaction leads to stereospecific inhibition of polymer formation by HbS. In other words, binding of these ligands to the αF helix induces a conformation change, perturbs the αF helix, and abrogates interactions between HbS, thereby weakening the polymer and preventing sickling. While it was previously believed that hydrogen-bonding moieties, such as an esters or amide, methyl hydroxyl, or a charged sulphate or phosphate group, on the compounds was necessary to make a strong interaction to produce the desired pharmacodynamic effect, the present invention discloses that highly potent interactions can be made with compounds through entirely water-mediated or hydrophobic interactions alone. In addition to the surprising potency, compounds in this group also lack the negative drawbacks of other previous compounds with an additional moiety on the second ring, such as VZHE-039 and PP-14; the compounds have been observed to have rapid RBC partitioning, good oral bioavailability, impressive pharmacokinetics, and no signs of toxicity. In some versions of these compounds, one or more halogens replace hydrogen on either the benzaldehyde or second ring structures; these halogens do not interact with the & F-helix residues but instead have the potential to modify the metabolic pathway of compounds by limiting interactions with metabolic enzymes and/or eliminate potentially toxic metabolic intermediates.

Compounds disclosed herein are benzaldehydes with a second ring (e.g., pyridine, pyrimidine, etc.) that interacts directly with the αF helix of sickle hemoglobin (HbS) without any direct hydrogen-bond donor/acceptor group or substituent (e.g., ester, amide, hydroxyl, sulphate or phosphate groups). Binding of the compound to the αF helix of HbS prevents or decreases the interaction between HbS molecules, and thus prevent sickling of red blood cells (RBCs).

The compounds have a generic Formula I:

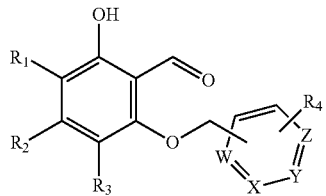

wherein:
  wherein W, X, Y, and Z are the same or different and are independently C or N, with the proviso that at least one of W, X, Y, and Z is an N, and $R_1$, $R_2$, $R_3$, and $R_4$ are the same or different and independently halogen or H.

Exemplary halogens include but are not limited to F and Cl.

Exemplary compounds include but are not limited to those having a formula

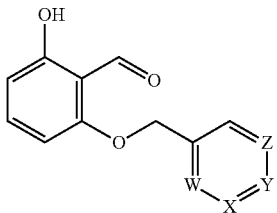

wherein W, X, Y and Z are the same or different and are independently C or N, and at least one of W, X, Y, and Z is N.

Compounds of this type include but are not limited to:

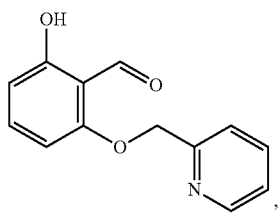

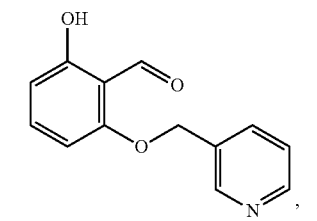

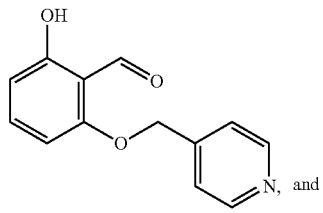

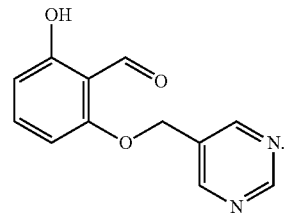

Additional exemplary compounds have the general formula

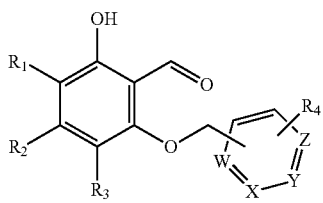

wherein W, X, Y and Z are the same or different and are independently C or N, and at least one of W, X, Y, and Z is N; $R_1$, $R_2$, $R_3$, and Ra are the same or different and independently halogen or H, and at least one of $R_1$, $R_2$, $R_3$, and $R_4$ is halogen. Exemplary halogens include but are not limited to F and Cl. Examples of these additional compounds include but are not limited to

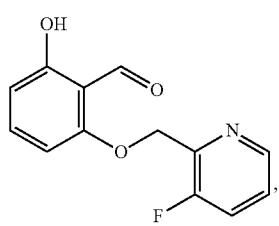

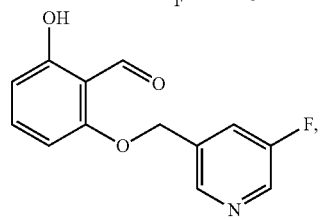

-continued

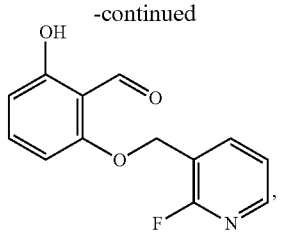

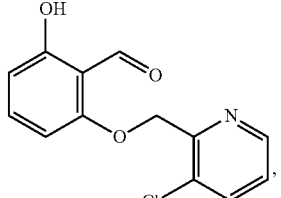

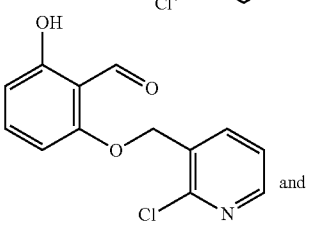 and

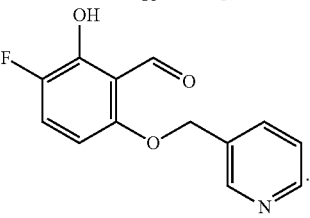

Pharmaceutically acceptable salts and oral prodrugs of the compounds are also encompassed. Examples of a suitable promoicty for an oral prodrug include but are not limited to thiazolidine, wherein the promoiety replaces the aldehyde to form an oral prodrug.

Exemplary Compounds

Exemplary compounds of the invention include but are not limited to:

("Reference A" in Table 1)

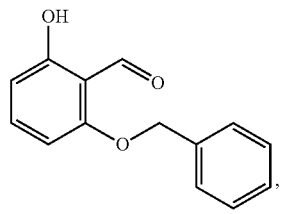

2-(benzyloxy)-6-hydroxybenzaldehyde ("Comp 1" in Table 1)

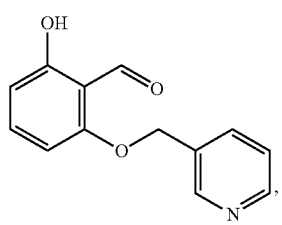

2-hydroxy-6-(pyridin-3-ylmethoxy)benzaldehyde

-continued ("Comp 2" in Table 1)

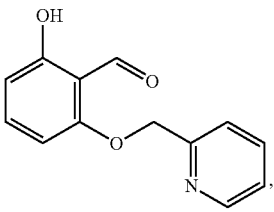

2-hydroxy-6-(pyridin-2-ylmethoxy)benzaldehyde ("Comp 3" in Table 1)

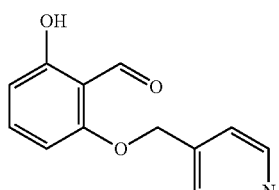

2-hydroxy-6-(pyridin-4-ylmethoxy)benzaldehyde ("Comp 4" in Table 1)

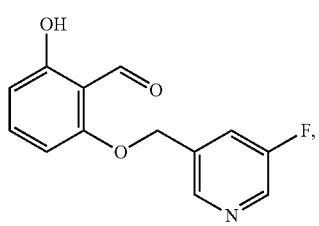

2-((5-fluoropyridin-3-yl)methoxy)-6-hydroxybenzaldehyde ("Comp 5" in Table 1)

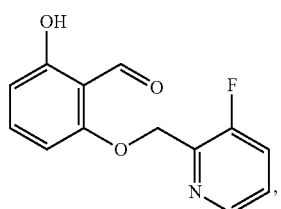

2-((3-fluoropyridin-2-yl)methoxy)-6-hydroxybenzaldehyde ("Comp 6" in Table 1)

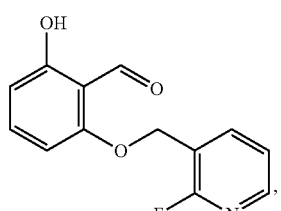

2-((2-fluoropyridin-3-yl)methoxy)-6-hydroxybenzaldehyde

-continued

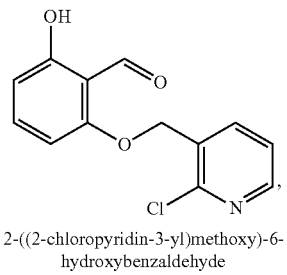

2-((2-chloropyridin-3-yl)methoxy)-6-hydroxybenzaldehyde ("Comp 7" in Table 1)

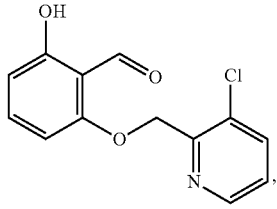

2-((3-chloropyridin-2-yl)methoxy)-6-hydroxybenzaldehyde ("Comp 8" in Table 1)

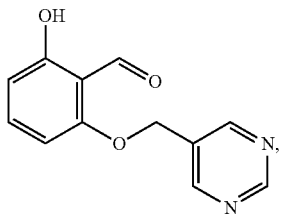

2-hydroxy-6-(pyrimidin-5-ylmethoxy)benzaldehyde ("Comp 10" in Table 1)

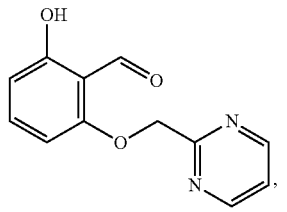

2-hydroxy-6-(pyrimidin-2-ylmethoxy)benzaldehyde ("Comp 11" in Table 1)

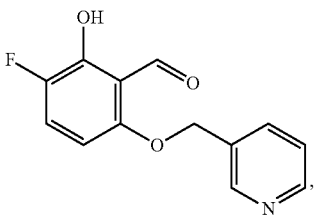

3-fluoro-2-hydroxy-6-(pyridin-3-ylmethoxy)benzaldehyde ("Comp 12" in Table 1)

These compounds rapidly partition into RBCs to bind to N-terminal valine amines in the HbS α-cleft via a Schiff-base interaction between the aldehyde moiety and the N-terminal αVal1 nitrogen of relaxed state hemoglobin. Mechanistically, the Schiff-base interaction stabilizes the relaxed state resulting in increased hemoglobin oxygen affinity and, consequently, anti-sickling activity. Like all aldehydes, the aldehyde moiety of the compounds is susceptible to rapid metabolism, e.g. by aldehyde oxidase, into the inactive carboxylate derivative that could potentially shorten the duration of the compounds pharmacologic effect. Consistently, the aromatic aldehyde anti-sickling agent 5-HMF was abandoned in human clinical studies because of its metabolic liability. In some aspect, the aldehyde group of the compounds presented herein is protected via an intramolecular bond with the adjacent ortho hydroxyl. The ortho hydroxyl also serendipitously positions the second ring to interact with the F helix.

Pharmaceutically Acceptable Salts

Pharmaceutically acceptable salts of the compounds are also encompassed. Examples of such salts include, but are not limited to, salts formed with inorganic acids (for example, hydrochloric acid (HCl), hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Oral Prodrugs

Oral prodrugs of the compounds are also encompassed. Oral prodrugs may be used, for example, to improve oral formulation and/or oral bioavailability or improve absorption characteristics and gastrointestinal tolerability. Examples of such prodrugs include, but are not limited to prodrugs formed by replacing the aldehyde group with a promoiety, such as thiazolidine, imine, acetal, hemiacetal, ester, or alcohol.

In some aspects, the compounds will be administered as prodrugs including but not limited to the following:

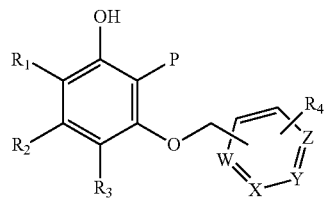

wherein W, X, Y and Z are the same or different and are independently C or N, with the proviso that at least one of W, X, Y, and Z is N, and $R_1$, $R_2$, $R_3$, and $R_4$ are the same or different and independently F, Cl or H, and P is a promoiety, such as a thiazolidine, imine, acetal, hemiacetal, ester, or alcohol.

In some aspects, the promoiety (P) is

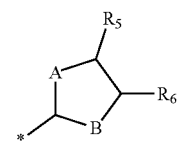

wherein A and B are the same or different and independently O, NH, S, OCH$_2$, NHCH$_2$, or SCH$_2$; and R$_5$ and R$_6$ are the same or different and independently COOH, COOR$_7$, CH$_2$OH, COCH$_3$ or —(CH$_2$)$_n$CH$_3$ where n=0-5 and R$_7$ is alkyl, aryl of heterocyclic; and where the bond marked with * bonds directly to a carbon of the benzene ring.

In some embodiment R$_5$ and R$_6$ can form a ring together as follows:

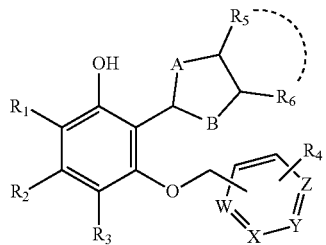

wherein the ring structure is an 3- to 8-membered ring with or without substitution.

In some aspects, the compound may be administered as a prodrug including but not limited to the following:

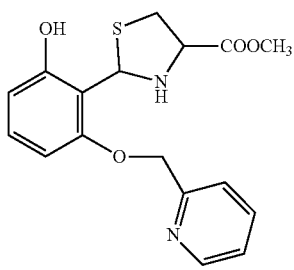

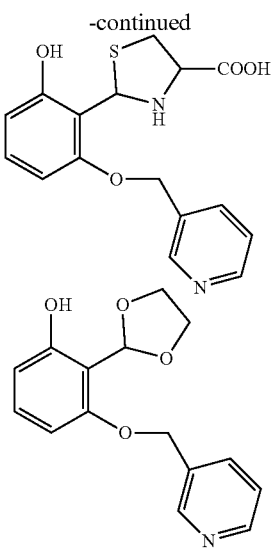

An example scheme for making a prodrug disclosed herein is as follows:

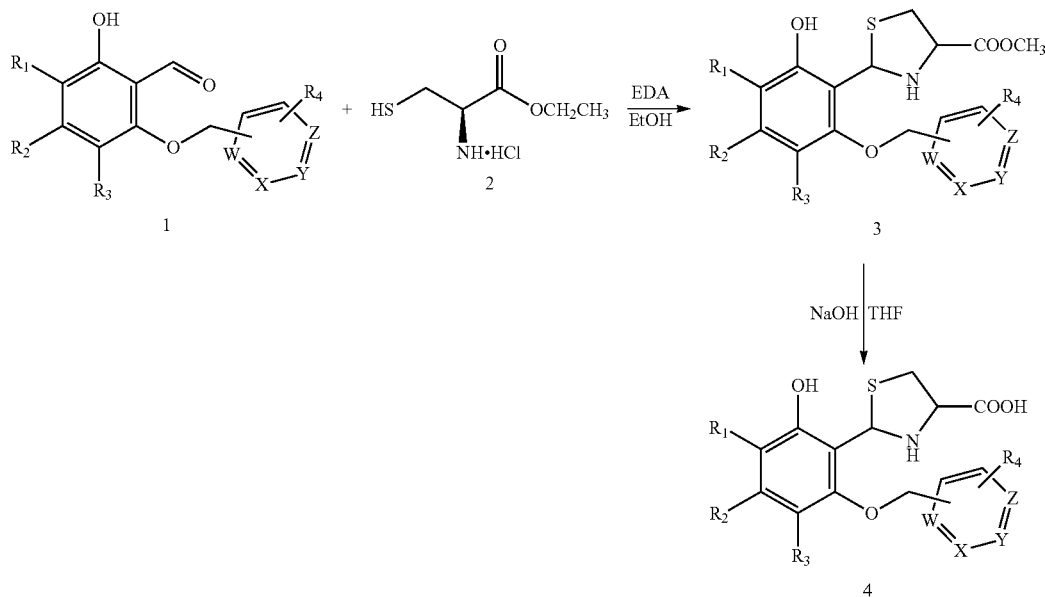

wherein W, X, Y and Z are the same or different and are independently C or N, with the proviso that at least one of W, X, Y, and Z is N, and R$_1$, R$_2$, R$_3$, and R$_4$ are the same or different and independently F, Cl or H.

A typical synthesis will involve the condensation of the benzaldehyde, 1 with equimolar L-cysteine ethyl ester, 2 in the presence of N-ethyldiisopropylamine hydrochloride (EDA) or triethyl amine (NET3) to yield the ethyl ester prodrug, 3. Hydrolysis of the ethyl ester protecting group of 3 with sodium hydroxide will yield the acid prodrug, 4.

Advantages of the Compounds

The compounds described herein exhibit improved pharmacologic activity, i.e., more potency and/or increased (lengthened, longer-lasting, etc.) half-lives, and/or improved bioavailability under physiological conditions (e.g., in 1, 2, 3, 4, 5, 6, 7, 8, 9, or 10-fold or more greater potency circulation, in blood, etc.) compared to other benzaldehyde compounds. For example, the compounds exhibit in vivo half-lives of at least about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5 or 12.0 hours, or even longer, e.g. about 12 to 60 hours, i.e. about 12, 14, 16, 18, 20, 22, 24, 26, 28, 30, 40, 50, or 60 hours. In some aspects, compared to vanillin or TD-7, the compounds exhibit 1, 2, 3, 4, 5, 6, 7, 8, 9, or 10-fold or more greater potency in terms of preventing RBC sickling and/or the formation of HbS polymers. In some aspects, compared to INN-310 and TD-7, the compounds exhibit 1, 2, 3, 4, 5, 6, 7, 8, 9, or 10-fold or more greater potency of polymer destabilizing effects or direct inhibition of HbS polymerization; Voxelotor demonstrates no direct inhibition of HbS polymerization. In some aspects, compared to VZHE-039, the compounds are safe to be administered at clinically relevant blood levels without toxicity, e.g., hepatocyte hypertrophy or apoptosis. In some aspects, compared to PP-14, the compounds do not have metabolically labile substituents that metabolize into charges species, e.g. carboxylic acid, that can reduce RBC membrane permeability. Thus, in some aspects, the compositions comprising the compounds are administered less frequently and/or at lower doses than would be required for prior art compounds, yet the same or an increased level of beneficial effects is experienced by subjects receiving the compounds. In some aspects, the compositions comprising the compounds can be administered to clinically beneficial levels without causing toxicity.

Exemplary Methods of Treatment Using the Compounds

The compounds described are used to treat or prophylactically treat diseases and/or conditions related to SCD and other diseases/conditions described below. As used herein, "prophylactically treat" ("prophylactic treatment", "prophylactically treating" etc.) and "prevent" ("prevention", "preventing" etc.) refer to warding off or averting the occurrence of at least one symptom of a disease or unwanted condition (such as at least one symptom of SCD), by prophylactic administration of a composition comprising at least one compound as described herein, to a subject in need thereof. Generally, "prophylactic" or "prophylaxis" relates to a reduction in the likelihood of the patient developing a disorder or a symptom of a disorder. Typically, the subject is considered by one of skill in the art to be at risk of or susceptible to developing at least one symptom of the disease or unwanted condition or is considered to be likely to develop at least one symptom of the disease/condition in the absence of medical intervention. In some aspects, for "prevention" or "prophylactic treatment", administration occurs before the subject has, or is known or confirmed to have, symptoms of the disease (condition, disorder, syndrome, etc.; unless otherwise indicated, these terms are used interchangeably herein). In other words, symptoms may not yet be overt or observable, or may be very "early stage" symptoms. The subject may be considered at risk due to a variety of factors, including but not limited to: genetic predisposition; evidence of "early" symptoms; tests such as blood tests, etc. In such aspects, treatment of the subject may prevent the noxious or harmful effects or outcomes (results) of full blown disease. "Prevention" or "prophylactic treatment" of a disease or condition may involve completely preventing the occurrence of detectable symptoms, or, alternatively, may involve lessening or attenuating the degree, severity or duration of at least one symptom of the disease that would otherwise occur in the absence of the medical interventions provided herein.

"Treat" (treatment, treating, etc.) as used herein refers to administering at least one composition comprising a compound as described herein, to a subject that already exhibits at least one symptom of a disease such as SCD. In other words, at least one parameter that is known to be associated with the disease has been measured, detected, experienced or observed in the subject. For example, the symptom may be the primary pathophysiology of RBC sickling associated with sickle cell disease. In addition, the compounds disclosed herein ameliorate several of the cascading secondary adverse events of SCD, including adhesion of RBCs to tissue endothelium, oxidative stress, hemolysis of RBCs, decreased vascular NO bioavailability, vaso-occlusion, impaired microvascular blood flow, increased blood pressure, stroke, and painful crises, e.g., due to polymerization of RBCs. For example, the compounds generally do one or more of the following: increase $O_2$-affinity of HbS; decrease fiber formation; reduce sickle cell mechanical fragility; reduce RBC hemolysis; attenuate hypoxia-induced cell necrosis and apoptosis; improve microvascular function (e.g. from sequelae of SCD or during recovery from hemorrhagic shock); results in hemodynamic and oxygenation benefits during hypoxia (e.g. maintenance of blood pressure and heart rate; preservation of microvascular blood flow; reduction in heart and brain hypoxia areas); reduce pain or the frequency of pain crises; decrease lactate dehydrogenase and/or RBC hemolysis; reduce diastolic blood pressure; increase blood oxygen levels ($S_pO_2$) during hypoxia challenge, etc.

"Treatment" of a disease involves the lessening or attenuation, or in some instances, the complete eradication, of at least one symptom of the disease that was present prior to or at the time of administration of the composition.

Exemplary Compositions and Methods of Administration

Provided herein are compositions comprising at least one compound as described herein, and methods of administering the same to treat e.g., SCD, hypoxia, etc. Implementation of the methods generally involves identifying patients suffering from or at risk of developing a disease or condition described herein (for example SCD or hypoxia), and administering a composition as described herein by an appropriate route. The exact dosage to be administered may vary depending on the age, gender, weight and overall health status of the individual patient, severity of disease symptoms, or on other treatments being received by the patient, as well as the extent or progression of the disease condition being treated and the precise etiology of the disease. However, in general for administration to mammals (e.g. humans), sufficient composition is administered to achieve dosages in the range of from about 0.1 to about 1000 mg or more per kg of body weight per 24 hr., e.g. from about 1 to about 500 mg. 5 to 100, or 10-50 mg per kg of body weight per 24 hr. Generally, a therapeutically effective dose is from about 20 to about 150 mg per kg of body weight per 24 hr. The dose will vary with the route of administration, the bioavailability, and the particular formulation that is administered, as well as according to the nature of the malady that is being prevented or treated.

The compositions are generally administered in a pharmaceutically acceptable formulation which includes suitable excipients, elixirs, binders, and the like (generally referred to as "pharmaceutically and physiologically acceptable carriers"), which are pharmaceutically acceptable and compatible with the active ingredients. The prodrugs or derivatives may be present in the formulation as pharmaceutically acceptable salts (e.g. alkali metal salts such as sodium, potassium, calcium or lithium salts, ammonium, etc.) or as other complexes. It should be understood that the pharmaceutically acceptable formulations include solid, semi-solid, and liquid materials conventionally utilized to prepare solid, semi-solid and liquid dosage forms such as tablets, capsules, liquids, acrosolized dosage forms, and various injectable forms (e.g., forms for intravenous administration), etc. Suitable pharmaceutical carriers include but are not limited to inert solid diluents or fillers, sterile aqueous solutions and various organic solvents. Examples of solid carriers (diluents, excipients) include lactose, starch, conventional disintegrating agents, coatings, lactose, terra alba, sucrose, talc, gelatin, agar, pectin, acacia, magnesium stearate, stearic acid and lower alkyl ethers of cellulose. Examples of liquid carriers include but are not limited to various aqueous or oil based vehicles, saline, dextrose, glycerol, ethanol, isopropanol, phosphate buffer, syrup, peanut oil, olive oil, phospholipids, fatty acids, fatty acid amines, polyoxyethylene, isopropyl myristate, ethyl cocoate, octyl cocoate, polyoxyethylenated hydrogenated castor oil, paraffin, liquid paraffin, propylene glycol, celluloses, parabens, stearyl alcohol, polyethylene glycol, isopropyl myristate, phenoxyethanol, and the like, or combinations thereof. Water may be used as the carrier for the preparation of compositions which may also include conventional buffers and agents to render the composition isotonic. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. In addition, the composition may contain minor amounts of auxiliary substances such as wetting or emulsifying agents, pH buffering agents, and the like. Similarly, the carrier or diluent may include any sustained release material known in the art, such as glycerol monostearate or glycerol distearate, alone or mixed with wax. Other potential additives and other materials (preferably those which are generally regarded as safe [GRAS]) include: colorants; flavorings; surfactants (TWEEN®, oleic acid, etc.); and solvents, stabilizers, binders or encapsulants (lactose, liposomes, etc.). Preservatives such as methyl paraben or benzalkium chloride may also be used. Depending on the formulation, it is expected that the active components (e.g. at least one prodrug or derivative) will be present at about 1% to about 99% of the composition and the vehicular "carrier" will constitute about 1% to about 99% of the composition. The pharmaceutical compositions of the present disclosure may include any suitable pharmaceutically acceptable additives or adjuncts to the extent that they do not hinder or interfere with the therapeutic effect(s) of the composition. Still other suitable formulations for use in the present disclosure can be found, for example in Remington's Pharmaceutical Sciences 22nd edition, Allen, Loyd V., Jr editor (September 2012); and Akers, Michael J. Sterile Drug Products: Formulation, Packaging, Manufacturing and Quality; publisher Informa Healthcare (2010).

The compositions (preparations) of the present disclosure are formulated for administration by any of the many suitable means which are known to those of skill in the art, including but not limited to: orally, by injection, rectally, by inhalation, intravaginally, intranasally, topically, as eye drops, via sprays, transdermally, sublingually, by rectal and buccal delivery, by inhalation of an aerosol, by microneedle delivery, etc. In some aspects, the mode of administration is oral, by injection or intravenously, preferably via an orally administered pill.

The administration of the compound of the present disclosure may be intermittent, or at a gradual or continuous, constant or controlled rate (e.g. in a sustained release formulation which further extends the time of bioavailability). In addition, the time of day and the number of times per day that the pharmaceutical formulation is administered vary and are best determined by a skilled practitioner such as a physician. Generally, the compounds are administered at least once a day, and may be administered e.g., 2, 3, 4, or more times per day. During a crisis, administration may be more frequent.

Administration of the compound by any means may be carried out as a single mode of therapy, or in conjunction with other therapies and treatment modalities, e.g., antibiotics, pain medication, hydroxyurea, vaccinations, blood transfusions, provision of supplemental oxygen, gene therapy, nitric oxide, drugs to boost fetal hemoglobin production, statins, etc. In addition, if disease sequalae includes other morbidities, e.g. a heart condition, then additional treatments for heart disease may be provided, including surgery. Other treatment options include various neutraceuticals, diet regimens, exercise, etc. "In conjunction with" refers to both administration of a separate preparation of the one or more additional agents, and to inclusion of the one or more additional agents in a composition of the present disclosure.

The subject to whom the composition is administered is generally a mammal, frequently a human, but this is not always the case. Veterinary applications of this technology are also contemplated, e.g., for companion pets (cats, dogs, etc.), or for livestock and farm animals, for horses, and even for "wild" animals that have special value or that are under the care of a veterinarian, e.g., animals in preserves or zoos, injured animals that are being rehabilitated, etc.

Diseases and Conditions that are Treated

In some aspects, the disease or condition that is prevented or treated as described herein is sickle cell disease and pathophysiologies associated with SCD, such as RBC sickling. In addition, the compounds ameliorate cascading secondary adverse events, including adhesion of RBCs to tissue endothelium, oxidative stress, hemolysis of RBCs, decreased vascular NO bioavailability, vaso-occlusion, impaired microvascular blood flow, increased blood pressure, stroke, and painful crises. In addition, the compounds increase $O_2$-affinity of HbS, decrease fiber formation, reduce sickle cell mechanical fragility, and reduce RBC hemolysis.

In other aspects, the compounds are used to treat or prevent symptoms of hypoxia that is or is not related to SCD. As used herein hypoxia (also known as hypoxiation) is a condition in which the body or a region of the body is deprived of adequate oxygen supply at the tissue level. Hypoxia is classified as either generalized, affecting the whole body, or local, affecting a region of the body. There are four types of hypoxia: (1) the hypoxemic type, in which the oxygen pressure in the blood going to the tissues is too low to saturate the hemoglobin; (2) the anemic type, in which the amount of functional hemoglobin is too small, and hence the capacity of the blood to carry oxygen is too low; (3) the stagnant type, in which the blood is or may be normal but the flow of blood to the tissues is reduced or unevenly distributed; and (4) the histotoxic type, in which the tissue and/or cells are poisoned and are therefore unable to make proper use of oxygen. Diseases of the blood, the heart and circulation, and the lungs may all produce some form of hypoxia.

Generalized hypoxia occurs, for example, in healthy people when they ascend to high altitude, where it causes altitude sickness leading to potentially fatal complications such as high-altitude pulmonary edema (HAPE) and high altitude cerebral edema (HACE). Hypoxia also occurs in healthy individuals when breathing mixtures of gases with a low oxygen content, e.g. while diving underwater or when in outerspace, and especially when using closed-circuit rebreather systems that control the amount of oxygen in the supplied air. Hypoxia also occurs as a consequence of preterm birth in the neonate due to immature lung development. Hypoxia resulting from ischemia (insufficient blood flow to a tissue or organ), is referred to as 'ischemic hypoxia' and is caused by e.g. an embolic event, a heart attack that decreases overall blood flow, or trauma to a tissue that results in damage, or may be purposefully induced in some medical procedures, e.g. implantation of a stent, application of a tourniquet, etc. Diseases such as peripheral vascular disease can cause local hypoxia. Other causes include alterations in respiratory drive, such as in respiratory alkalosis, physiological or pathological shunting of blood, diseases interfering in lung function resulting in a ventilation-perfusion mismatch, such as a pulmonary embolus, or alterations in the partial pressure of oxygen in the environment or lung alveoli. When hemoglobin is deficient, anemia can result and can cause 'anemic hypoxia' if tissue perfusion is decreased. Carbon monoxide poisoning can cause hypoxia, either acutely, as with smoke intoxication, or over a period of time, as with cigarette smoking or exposure to smog. Certain odorless asphyxiant gases (e.g. nitrogen, methane, etc.) induce hypoxia as does cyanide poisoning and the formation of methemoglobin e.g. by ingesting sodium nitrite or certain other drugs and chemicals. The compounds described herein are used to prevent or treat symptoms of one or more of any of these hypoxia-related conditions. In addition, the compounds attenuate hypoxia-induced cell necrosis and apoptosis, improve microvascular function during resuscitation from hemorrhagic shock, result in hemodynamic and oxygenation benefits during hypoxia (e.g. maintenance of blood pressure and heart rate; preservation of microvascular blood flow; reduction in heart and brain hypoxia areas, etc.), and provide improvement in several clinical symptoms, including reduced pain, decreased lactate dehydrogenase and/or RBC hemolysis, reduction in diastolic blood pressure, and an increase in blood oxygen levels ($S_pO_2$) during hypoxia challenge.

Methods of Making the Compounds

A generic scheme for making the compounds disclosed herein is depicted below in Scheme I. Briefly, substituted hydroxybenzaldehyde and either substituted chloromethylpyridine or substituted bromomethylpyridine were reacted together under basic conditions at room temperature for 2 hours, and then at 60° C. for 4-6 hours to give Compounds 1-13 in 9-47% yields.

Scheme 1

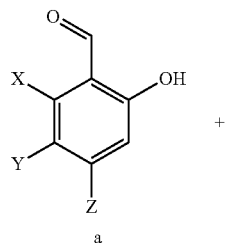

a1: X = OH, Y = H, Z = H
a2: X = F, Y = H, Z = F
a3: X = OH, Y = F, Z = H

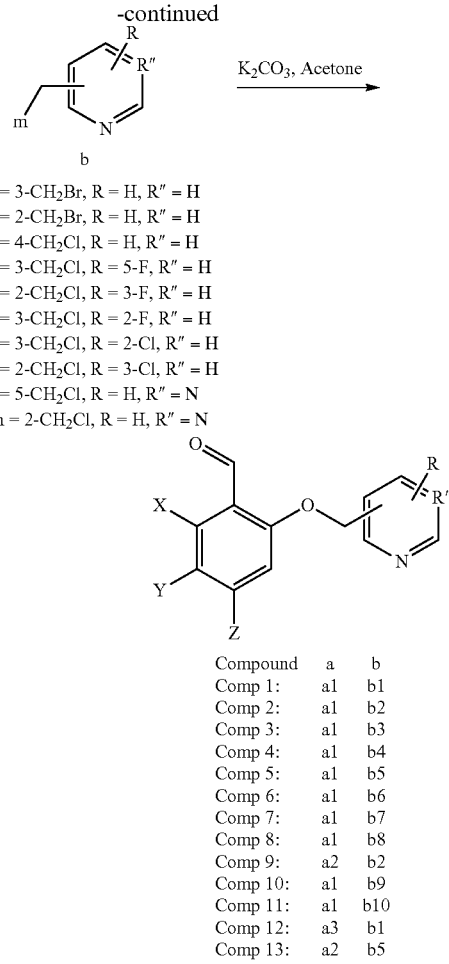

b1: m = 3-CH$_2$Br, R = H, R″ = H
b2: m = 2-CH$_2$Br, R = H, R″ = H
b3: m = 4-CH$_2$Cl, R = H, R″ = H
b4: m = 3-CH$_2$Cl, R = 5-F, R″ = H
b5: m = 2-CH$_2$Cl, R = 3-F, R″ = H
b6: m = 3-CH$_2$Cl, R = 2-F, R″ = H
b7: m = 3-CH$_2$Cl, R = 2-Cl, R″ = H
b8: m = 2-CH$_2$Cl, R = 3-Cl, R″ = H
b9: m = 5-CH$_2$Cl, R = H, R″ = N
b10: m = 2-CH$_2$Cl, R = H, R″ = N

| Compound | a | b |
|---|---|---|
| Comp 1: | a1 | b1 |
| Comp 2: | a1 | b2 |
| Comp 3: | a1 | b3 |
| Comp 4: | a1 | b4 |
| Comp 5: | a1 | b5 |
| Comp 6: | a1 | b6 |
| Comp 7: | a1 | b7 |
| Comp 8: | a1 | b8 |
| Comp 9: | a2 | b2 |
| Comp 10: | a1 | b9 |
| Comp 11: | a1 | b10 |
| Comp 12: | a3 | b1 |
| Comp 13: | a2 | b5 |

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely." "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLE

Recently, we, serendipitously, discovered a set of benzaldehydes that exhibit highly potent polymer destabilizing effects, but without any chemical substituent on the second ring (pyridine or benzene) that would be expected to be needed to make strong interactions with the αF-helix residues, other than possibly the replacement of a hydrogen with a halogen (e.g., F or Cl). Initially, these compounds were synthesized and tested on the basis that they represented a chemical scaffold for the discovery of new polymer destabilizing benzaldehydes by screening new chemical substituents to add to the second ring, but it was presumed that they would have very weak polymer destabilizing effects, similar to INN-310, since they lack a chemical substituent to make strong interactions with the αF helix, as with VZHE-039 and PP-14. However, unexpectedly, these compounds can make very strong interactions with the αF-helix residues that are either entirely water-mediated directly through a pyridine, or alternatively a pyrimidine or triazine nitrogen, or even entirely hydrophobic via a benzene ring. Although in some aspects, halogens replace hydrogen on the ring structures, these halogens do not interact with the αF-helix residues, but instead are intended to possibly limit or modify interactions with metabolic enzymes and/or eliminate possibly toxic metabolic intermediates. The unexpected result appears to be the consequence of slight changes in the orientation of the compounds in the Hb a cleft with the addition of the ortho hydroxyl on the benzaldehyde ring to replace the meta methoxy of INN-310. This, fortuitously, moved the second ring structure in position to make its own strong interactions with αF-helix residues without any hydrogen-bond donor/acceptor substituent required. On the contrary, replacement of the ortho hydroxyl on the benzaldehyde with a fluorine (Compound 9 and 13) completely negates the polymer destabilization effects of the compounds. Also, addition of a meta fluorine next to the ortho hydroxyl on the benzaldehyde (Compound 12) significantly reduced the potency of polymer inhibition.

Therefore, a series of novel analogues with unexpected polymer destabilizing effects and surprising potency has been prepared. In fact, Compounds 1 and 2 (Table 1) are the most potent polymer destabilizers discovered to date, consistently demonstrating rapid partitioning into RBCs and robust and sustained inhibition of RBC sickling in complete anoxia, improving on the potency of VZHE-039 and PP-14. Compounds 1, 2, and 5 have also demonstrated acceptable absorption, distribution, metabolism and elimination (ADME) properties without metabolic lability, consistent with a viable oral small molecule human drug for the treatment of sickle cell disease. On the contrary, Reference Compound A, which makes entirely hydrophobic interactions with the αF-helix via a benzene ring and exhibits potent polymer destabilizing effects, is not bioavailable. Compounds 1, 2, and 5 have each demonstrated safety in non-clinical toxicology above anticipated therapeutic drug levels without hepatotoxicity, indicating an acceptable therapeutic window for a human clinical trial. These are the first polymer destabilizing benzaldehydes with properties that are suitable for advancing into a human trial. Conversely, of hundreds of compounds tested with different chemical substituents on the second ring, no viable drug candidates were identified due to various liabilities relating to the second ring substituent.

Results and Discussion

Synthesis/Chemistry

Compounds 1-13 in Table 1 were synthesized as shown in scheme 4. Briefly, substituted hydroxybenzaldehyde and either substituted chloromethylpyridine or substituted bromomethylpyridine were reacted together under basic conditions at room temperature for 2 hours, and then at 60° C. for 4-6 hours to give Compounds 1-13 in 9-47% yields. A detailed description of the synthesis of each compound is reported in the experimental section. The synthesis of comparator molecules in Table 2, such as TD-7, INN-310, PP-14, and Voxelotor, have been reported in the literature.

Scheme 1

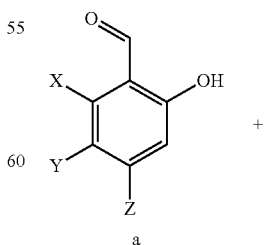

a
a1: X = OH, Y = H, Z = H
a2: X = F, Y = H, Z = F
a3: X = OH, Y = F, Z = H

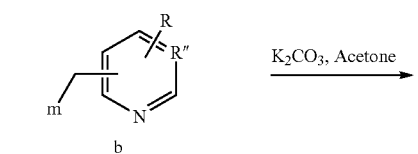

b1: m = 3-CH₂Br, R = H, R″ = H
b2: m = 2-CH₂Br, R = H, R″ = H
b3: m = 4-CH₂Cl, R = H, R″ = H
b4: m = 3-CH₂Cl, R = 5-F, R″ = H
b5: m = 2-CH₂Cl, R = 3-F, R″ = H
b6: m = 3-CH₂Cl, R = 2-F, R″ = H
b7: m = 3-CH₂Cl, R = 2-Cl, R″ = H
b8: m = 2-CH₂Cl, R = 3-Cl, R″ = H
b9: m = 5-CH₂Cl, R = H, R″ = N
b10: m = 2-CH₂Cl, R = H, R″ = N

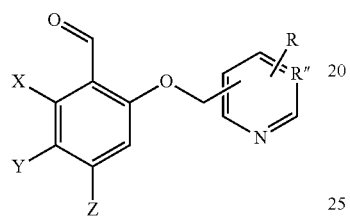

| Compound | a | b |
|---|---|---|
| Comp 1: | a1 | b1 |
| Comp 2: | a1 | b2 |
| Comp 3: | a1 | b3 |
| Comp 4: | a1 | b4 |
| Comp 5: | a1 | b5 |
| Comp 6: | a1 | b6 |
| Comp 7: | a1 | b7 |
| Comp 8: | a1 | b8 |
| Comp 9: | a2 | b2 |
| Comp 10: | a1 | b9 |
| Comp 11: | a1 | b10 |
| Comp 12: | a3 | b1 |
| Comp 13: | a2 | b5 |

Table 1. Structures of Exemplary Target Compounds

| Compound | Compound Structure and Name |
|---|---|
| Reference A | 2-(benzyloxy)-6-hydroxybenzaldehyde |
| Comp 1 | 2-hydroxy-6-(pyridin-3-ylmethoxy)benzaldehyde |
| Comp 2 | 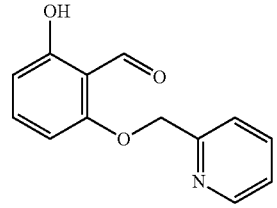 [SMILES: O=Cc1c(O)cccc1OCc1ccccn1] 2-hydroxy-6-(pyridin-2-ylmethoxy)benzaldehyde |
| Comp 3 | 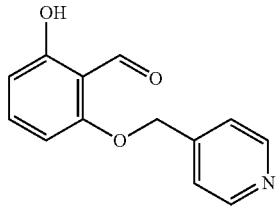 [SMILES: O=Cc1c(O)cccc1OCc1ccncc1] 2-hydroxy-6-(pyridin-4-ylmethoxy)benzaldehyde |
| Comp 4 | 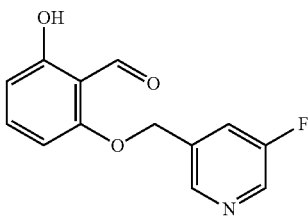 [SMILES: O=Cc1c(O)cccc1OCc1cncc(F)c1] 2-((5-fluoropyridin-3-yl)methoxy)-6-hydroxybenzaldehyde |
| Comp 5 | 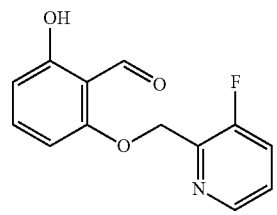 [SMILES: O=Cc1c(O)cccc1OCc1ncccc1F] 2-((3-fluoropyridin-2-yl)methoxy)-6-hydroxybenzaldehyde |
| Comp 6 | 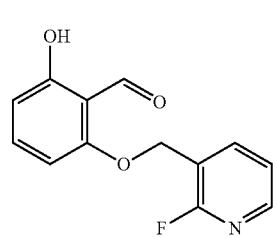 2-((2-fluoropyridin-3-yl)methoxy)-6-hydroxybenzaldehyde |

-continued

| Compound | Compound Structure and Name |
|---|---|
| Comp 7 | 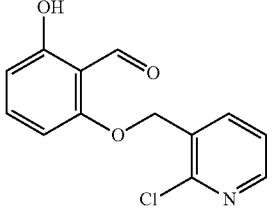 [SMILES: O=Cc1c(O)cccc1OCc1cccnc1F]<br>2-((2-chloropyridin-3-yl)methoxy)-6-hydroxybenzaldehyde |
| Comp 8 | 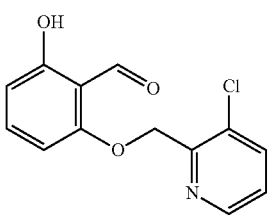 [SMILES: O=Cc1c(O)cccc1OCc1ncccc1Cl]<br>2-((3-chloropyridin-2-yl)methoxy)-6-hydroxybenzaldehyde |
| Comp 9 | 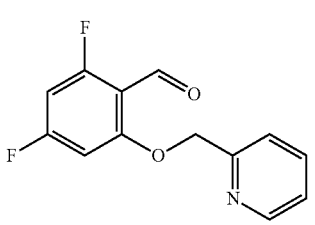 [SMILES: O=Cc1c(F)cc(F)cc1OCc1ccccn1]<br>2,4-difluoro-6-(pyridin-2-ylmethoxy)benzaldehyde |
| Comp 10 | 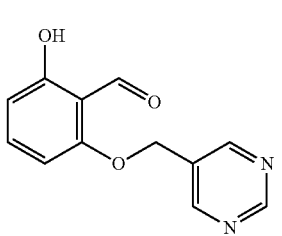 [SMILES: O=Cc1c(O)cccc1OCc1cncnc1]<br>2-hydroxy-6-(pyrimidin-5-ylmethoxy)benzaldehyde |
| Comp 11 | 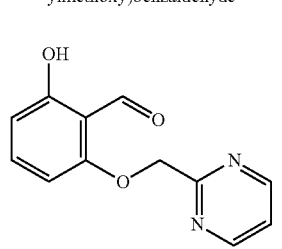<br>2-hydroxy-6-(pyrimidin-2-ylmethoxy)benzaldehyde |

-continued

| Compound | Compound Structure and Name |
|---|---|
| Comp 12 | 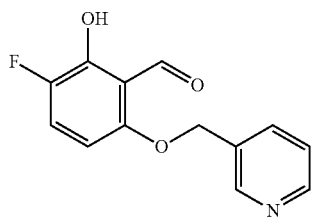 [SMILES: O=Cc1c(OCc2cccnc2)ccc(F)c1O]<br>3-fluoro-2-hydroxy-6-(pyridin-3-ylmethoxy)benzaldehyde |
| Comp 13 | 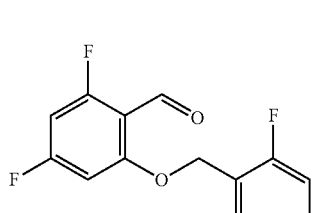<br>2,4-difluoro-6-((3-fluoropyridin-2-yl)methoxy)benzaldehyde |

TABLE 2

Structures of Comparator Molecules

| Compound | Compound Structure and Name |
|---|---|
| Voxelotor | 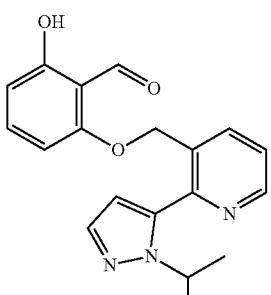 |
| INN-310 | 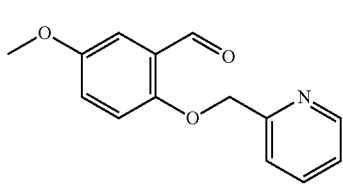 [SMILES: COc1ccc(OCc2ccccn2)c(C=O)c1] |
| TD-7 | 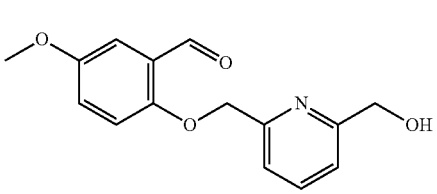 [SMILES: COc1ccc(OCc2cccc(CO)n2)c(C=O)c1] |

TABLE 2-continued

Structures of Comparator Molecules

| Compound | Compound Structure and Name |
|---|---|
| VZHE-039 | |
| PP-14 | 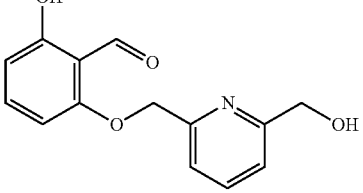 |

In Vitro Functional and Biological Assessment

Compounds 1-13 (Table 1) were studied with comparator molecules INN-310, TD-7, VZHE-039, PP-14, and Voxelotor (Table 2). The syntheses of the comparator molecules have been reported in the literature. All comparator molecules are aromatic aldehydes and are known to increase Hb affinity for oxygen with concomitant inhibition of hypoxia-induced RBC sickling. While PP-14 and VZHE-039 exhibit potent anti-sickling effects through direct polymer destabilization, Voxelotor, INN-310, and TD-7 show limited to no such effect.

Figure 2:
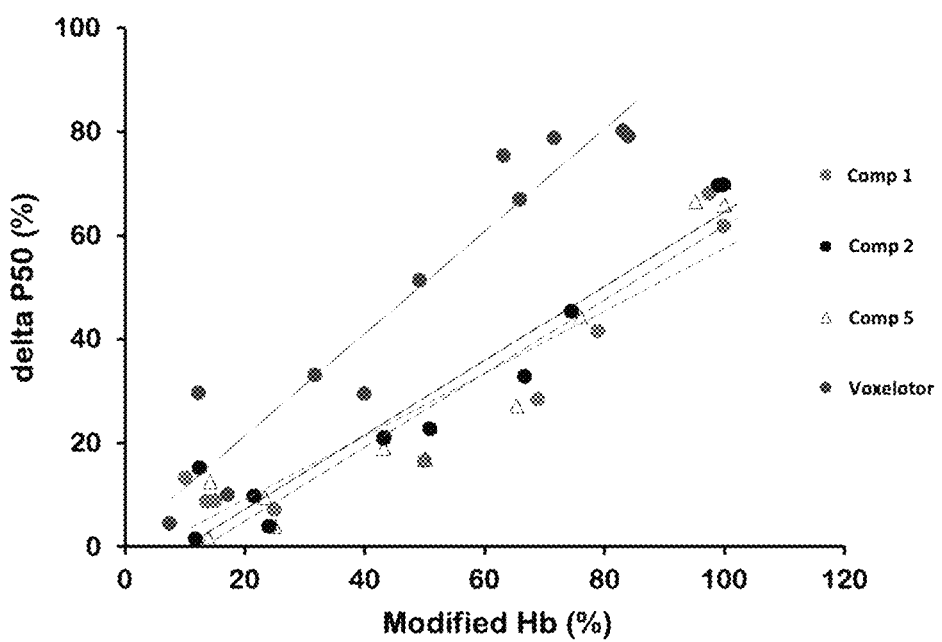
FIG. 2. Occupancy dependent p50 shift in human non-sickle blood.
Figure 3A:
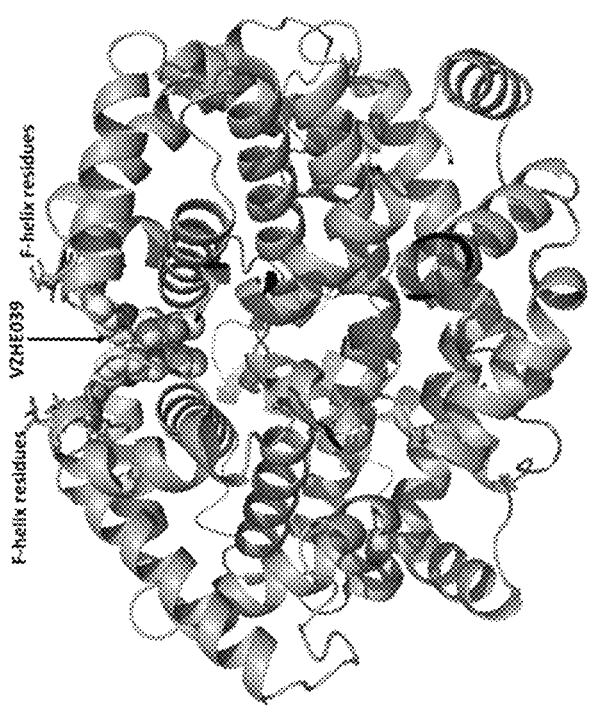
FIG. 3A-3G. Crystal structure of Hb in the $R_2$ conformation in complex with two molecules of Compounds 1, 2, 5, and 8 bound at the α-cleft. Structure of VZHE039 shown for comparative purpose. Hb is shown as cartoon; Compound 1, 2, 5 and 8 in sticks; F-helix residues in sticks; and water molecules as spheres.
Figure 3B:
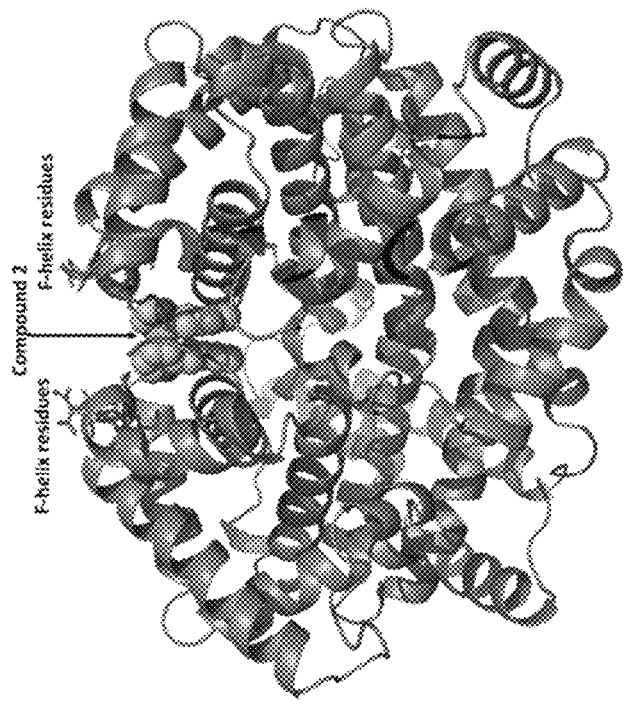
Figure 3D:
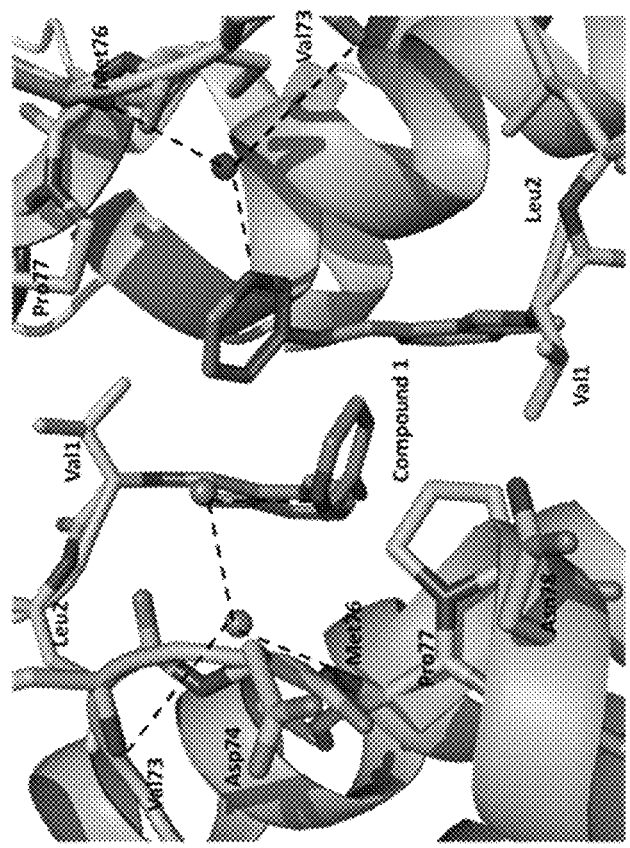
Figure 3C:
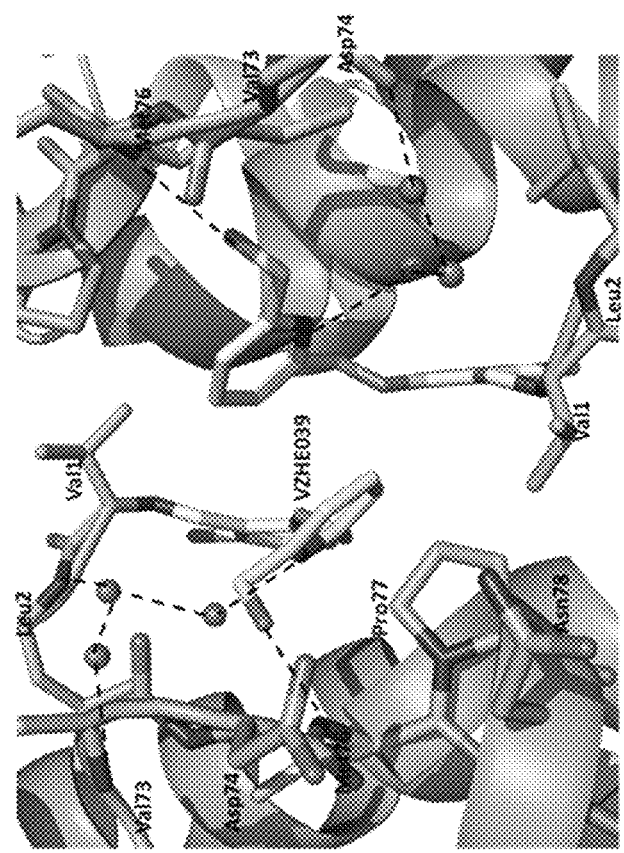
Figure 3F:
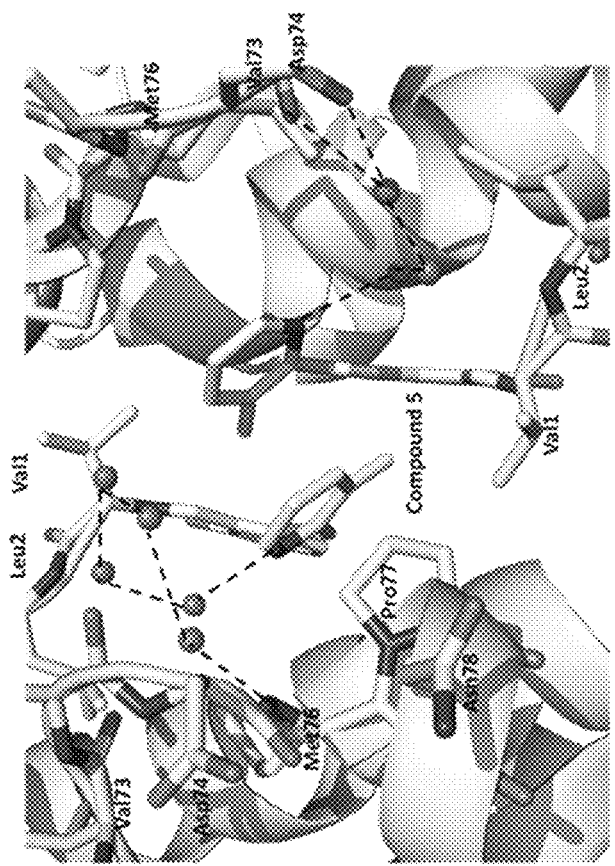
Figure 3E:
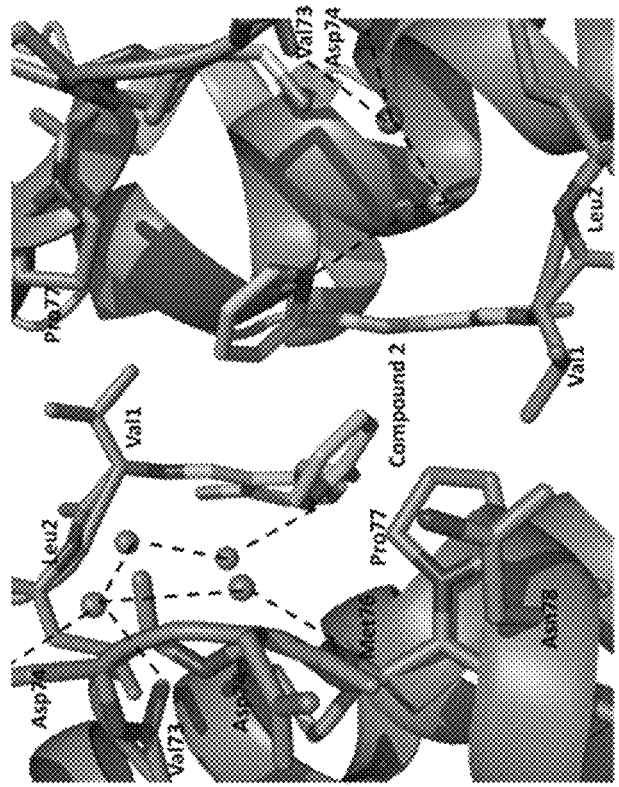
Figure 3G:
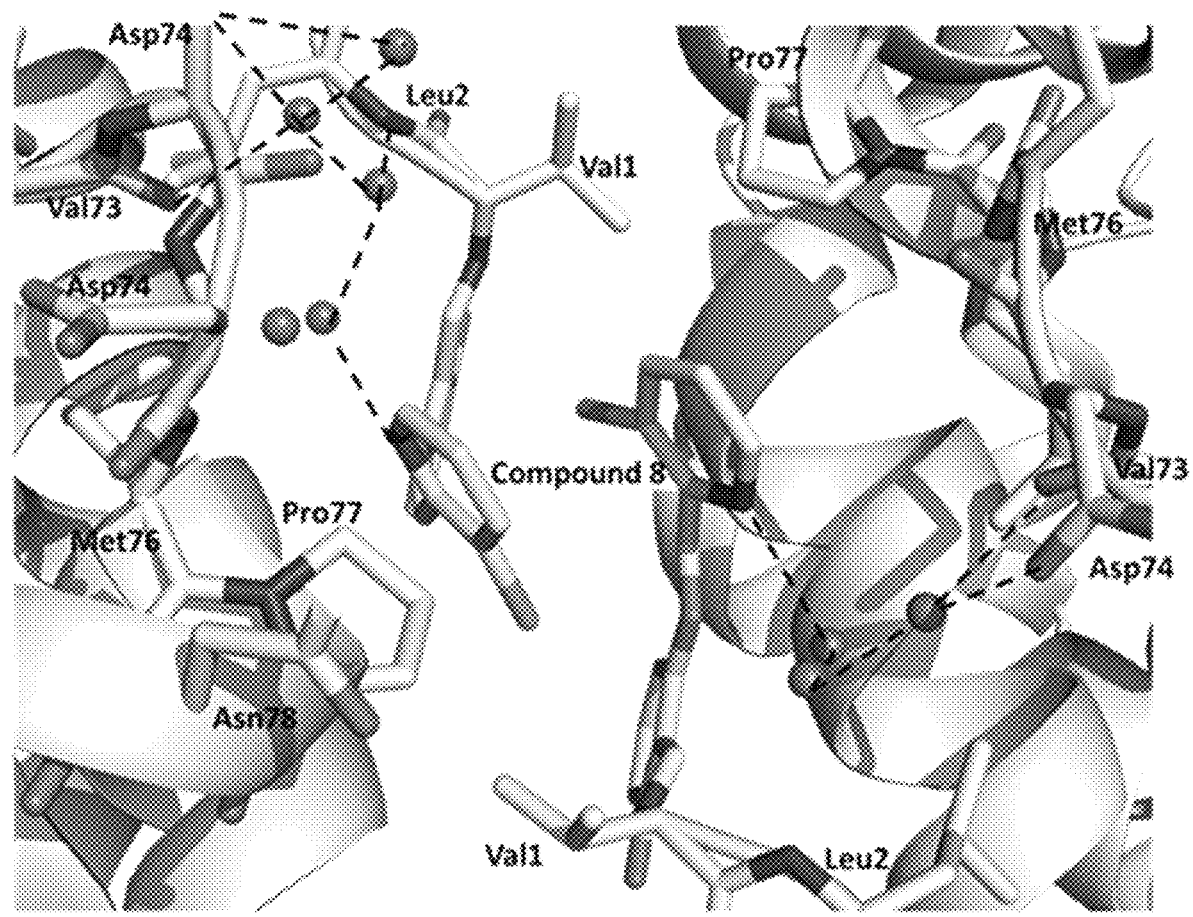

Compounds 1-13 formed adducts with Hb and exhibited potent sickle inhibition following incubation in hypoxia, and most compounds in the class, unexpectedly, also demonstrated potent polymer destabilizing effects with sickle inhibition in anoxia (Table 3). Comparatively, Voxelotor did not demonstrate any sickle inhibition in anoxic conditions. In anoxia time-course experiments (FIG. 2), Compounds 1 and 2 surprisingly demonstrated the most potent and sustained polymer destabilizing effects observed to date, generally at least as potent or more potent than compounds with chemical substituents that form direct interactions with the αF-helix surface residues, such as VZHE-039 and PP-14, among many others that have been tested. On the contrary, INN-310 demonstrated only weak potency in anoxia. Despite potent anti-sickling effects, Compounds 1, 2, and 5 exhibited relatively weak changes in p50 of Hb in human blood compared to Voxelotor (FIG. 2) at equivalent drug-Hb occupancy levels, demonstrating the relative importance of direct polymer destabilization to the efficacy of this class of compounds.

In partitioning studies, all compounds exhibited high partitioning ratios above 90% (Table 4), indicating that the compounds rapidly permeated the RBC membrane. Therefore, differences in fixed drug-Hb adducts reflect largely only differences in Hb binding affinity of each compound. The most potent compounds, Comp 1, 2, and 5, demonstrated greater than 90% Hb adducts after incubation at a 2 mM concentration in AA blood.

TABLE 3

Hemoglobin modification and sickle inhibition studies using blood suspensions from humans with homozygous SCD

| Compound ID | Hb Modification (%) | % Sickling Inhibition (Hypoxia) | % Sickling Inhibition (Anoxia) |
|---|---|---|---|
| Voxelotor | 92.3 ± 6.8 | 79.9 ± 6.2 | 1.5 ± 5.5 |
| INN-310 | 65.7 ± 6.0 | 69.9 ± 20.0 | 17.9 ± 7.0 |
| TD-7 | 72.5 | 80.6 ± 5.8 | 20.4 ± 2.9 |
| VZHE-039 | 90.7 ± 9.9 | 75.3 ± 14.3 | 68.9 ± 17.7 |
| PP-14 | 85.3 ± 11.3 | 83.1 ± 6.9 | 80.5 ± 17.4 |
| Comp 1 | 95.8 ± 6.2 | 74.8 ± 15.9 | 71.9 ± 16.0 |
| Comp 2 | 95.5 ± 5.7 | 72.8 ± 13.0 | 63.2 ± 17.2 |
| Comp 3 | 74.4 ± 10.6 | 54.1 ± 14.7 | 26.2 ± 8.6 |
| Comp 4 | 92.9 ± 9.8 | 64.3 ± 24.5 | 69.6 ± 13.4 |
| Comp 5 | 98.2 ± 2.5 | 66.6 ± 9.4 | 66.5 ± 21.1 |
| Comp 6 | 73.8 ± 15.4 | 67.1 ± 5.8 | 32.6 ± 28.5 |
| Comp 7 | 73.91 ± 9.8 | 36.1 ± 19.7 | 9.4 ± 10.7 |
| Comp 8 | 100.0 ± 0.0 | 69.7 ± 8.0 | 18.3 ± 8.4 |
| Comp 9 | 69.1 ± 11.8 | 68.1 ± 29.8 | 0 ± 5.6 |
| Comp 10 | 100.0 ± 0.0 | 76.6 ± 10.9 | 75.6 ± 18.5 |
| Comp 11 | 98.1 ± 3.2 | 67.4 ± 18.2 | 45.1 ± 10.8 |
| Comp 12 | 99.8 ± 0.4 | 68.6 ± 12.0 | 28.7 ± 6.9 |
| Comp 13 | 79.1 ± 10.3 | 63.6 ± 24.3 | −0.5 ± 2.7 |

Biological effects shown with compounds at 2 mM concentration, 4 biological replicates

TABLE 4

Hemoglobin modification, studies using non-sickling AA blood

| Compound ID | Fixed Adducts (%) | Unfixed Adduct (%) | Partitioning Ratio (%) |
|---|---|---|---|
| Voxelotor | 77.0 ± 3.8 | 80.3 ± 6.3 | 96.1 ± 3.7 |
| INN-310 | 82.0 ± 3.1 | 79.7 ± 4.3 | 103.0 ± 1.7 |
| TD-7 | 80.9 ± 2.5 | 73.5 ± 1.5 | 103.7 ± 7.5 |
| VZHE-039 | 90.9 ± 3.4 | 92.4 ± 5.6 | 98.5 ± 4.3 |
| PP-14 | 96.1 ± 1.1 | 91.8 ± 11.6 | 102.2 ± 8.0 |
| Comp 1 | 96.0 ± 1.9 | 97.4 ± 2.8 | 98.6 ± 2.8 |
| Comp 2 | 95.2 ± 2.3 | 96.3 ± 2.6 | 98.9 ± 2.9 |
| Comp 3 | 60.1 ± 3.0 | 60.0 ± 3.3 | 100.1 ± 0.9 |
| Comp 4 | 85.9 ± 7.1 | 88.8 ± 6.2 | 96.9 ± 5.73 |
| Comp 5 | 93.1 ± 3.3 | 95.8 ± 3.3 | 97.2 ± 3.2 |
| Comp 6 | 67.3 ± 12.1 | 67.1 ± 10.3 | 100.0 ± 2.8 |
| Comp 7 | 59.6 ± 5.7 | 60.2 ± 5.7 | 99.0 ± 3.1 |
| Comp 8 | 85.6 ± 2.5 | 84.8 ± 7.5 | 101.3 ± 6.3 |
| Comp 9 | 72.7 ± 4.1 | 69.4 ± 7.5 | 105.2 ± 5.9 |
| Comp 10 | 94.8 ± 2.8 | 96.3 ± 3.0 | 98.5 ± 2.7 |
| Comp 11 | 88.2 ± 2.1 | 87.7 ± 4.3 | 100.7 ± 3.0 |
| Comp 12 | 80.4 ± 9.1 | 80.8 ± 5.9 | 99.4 ± 4.2 |
| Comp 13 | 80.7 ± 4.8 | 78.4 ± 6.1 | 103.0 ± 2.9 |

Biological effects shown with compounds at 2 mM concentration, 6 biological replicates X-Ray Crystallography with Atomic Basis for the Hb Polymer Destabilizing Effects Compounds 1-13 were co-crystallized with liganded Hb (carbonmonoxy Hb or COHb) using low-salt condition. Only Compounds 1, 2, 5 and 8 resulted in X-ray diffraction quality crystals with Hb, leading to their structure determination at 1.9 Å to 2.1 Å resolutions. The ensuing tetrameric Hb-bound compound complex crystal structures, as expected were in the relaxed R2-state conformation, similar to the previously determined R2-state tetrameric Hb structures in complex with the comparator molecules INN-310, VZHE-039, PP-14, and Voxelotor.) The overall structures of all complexes were indistinguishable (RMSD 0.3-0.5 Å) when compared among themselves or with the native R2-state structure (PDB code 1BBB) or with the comparator Hb complex structures. Also, as expected, and similar to INN-310, VZHE-039, PP-14 (but unlike Voxelotor), two molecules of each compound bind in a symmetrical fashion at the α-cleft of the Hb tetramer with the aldehyde moieties forming Schiff-base interactions with the two αVal1 N-terminal amines from the α1- and α2-subunits, while also making several other protein interactions. Voxelotor only binds one molecule at the α-cleft (forms 1 Schiff-base interaction) due to its bulky nature that excludes two molecules from binding. The Schiff-base interaction of these compounds is consistent with the observed modification of Hb, which exhibits a different peak on cation exchange HPLC than unmodified Hb. Specific interactions with the protein involve the benzaldehyde and/or pyridine ring making both intra- and inter-subunit hydrophobic and/or hydrogen-bond (direct or water-mediated) interactions with αAla130, αSer131, αThr134, αThr134 and/or αLeu2. For the compounds that bind with two molecules (exception is Voxelotor), the pyridine rings of the two bound molecules also formed extensive face-to-face π-π stacking interactions with each other. The interactions with Hb, as previously reported for other benzaldehydes, serve to stabilize the relaxed state Hb, consistent with their ability to increase the oxygen affinity of Hb with concomitant oxygen-dependent anti-sickling effects as shown in Table 3.

Most importantly, and consistent with the compounds' oxygen-independent anti-sickling effects in completely anoxic conditions, Compounds 1, 2, 5, and 8, like VZHE-039 and PP-14 but not INN-310 and Voxelotor, also make hydrogen-bond interactions with the surface-located αF-helix residues (FIG. 3A-3G). As noted above, the &F-helix is important in stabilizing Hb polymers, and its perturbation as a result of interactions with the second ring of the benzaldehydes leads to direct polymer destabilization. Differences in the unique interactions of each compound with the αF-helix always correspond to the potency of polymer destabilizing effects as determined based on the sickling inhibition in anoxia. VZHE-039 and PP-14 have methylhydroxyl and carboxylester substituents, respectively, on the pyridine ring to make hydrogen-bond interactions with residues of the αF-helix. Despite not having any heteroatom-containing substituents on the pyridine ring, Compounds 1, 2, 5, and 8 unexpectedly make water-mediated interactions with the αF-helix residues through the pyridine nitrogen. Compound 1 involves very strong water-mediated hydrogen-bonding interactions with the F-helix residues through either 1 or 2 water molecules. Compounds 2, 5, and 8 make interactions with the αF-helix through at least 3 water molecules. Compound 1 thus appears to make the strongest hydrogen-bond interactions with the αF-helix residues, even when compared to VZHE-039 and PP-14, also explaining the high affinity of Compound 1 ($K_D$ of 0.06 mM vs 0.1 mM for VZHE-039 and 0.15 for PP-14). INN-310 only makes weak to moderate hydrophobic interaction with the αF-helix and no hydrogen-bond interactions, and exhibits only very weak polymer destabilizing effects with limited anti-sickling effect in anoxia. Hence why it is was previously expected that compounds in the present invention would not exhibit potent polymer destabilizing effects. In contrast, the bulky substituent of Voxelotor orients the pyridine moiety away from the αF-helix, explaining the complete absence of polymer destabilizing effects.

In Vivo Pharmacokinetics Assessments
Single Dose PK Study

Single-dose pharmacokinetics (PK) in male Sprague Dawley (SD) rats (n=4) were assessed for each compound, and the maximum or peak whole blood concentration and area under the curve are shown in Table 5. Compounds 1, 2, and 5 exhibited the greatest oral exposure levels observed to date for polymer destabilizing benzaldehydes, especially on a molar equivalent basis. While not shown, PP-14 rapidly metabolizes into its carboxylic acid metabolite upon oral administration.

TABLE 5

Summary of single-dose pharmacokinetic properties in rats

| Compound ID | $C_{max}$ (ng/ml) [μM] | $AUC_{0-\infty}$ (ng · h/mL) [μM * h] | $T_{1/2}$ (hours) |
| --- | --- | --- | --- |
| VZHE-039 | 102,120 [394] | 2,276,790 [8,782] | 8.4 |
| Comp 1 | 210,775 [919] | 3,992,235 [17,415] | 5.0 |
| Comp 2 | 219,599 [958] | 4,543,996 [19,822] | 9.7 |
| Comp 4 | 59,759 [242] | 830,811 [3,360] | 5.9 |
| Comp 5 | 85,965 [348] | 2,978,475 [12,047] | 8.8 |
| Comp 6 | 12,053 [49] | 179,894 [728] | 8.2 |
| Comp 8 | 20,035 [76] | 269,353 [1,022] | 9.5 |
| Comp 10 | 36,219 [157] | 693,278 [3,011] | 4.7 |

Single oral dose administered at 100 mg/kg

14-Day Repeat Dose PK Study

Repeat oral doses of each compound were administered by oral gavage for 14 days to male and female SD rats (n=3). Steady state peak drug concentrations and area under the curve for each compound is shown in Table 6. Compounds 2 and 5 exhibited the greatest oral exposure levels observed to date, especially on a molar equivalent basis. Oral exposure levels were of Compound 1 were similar to VZHE-039 and greater than Voxelotor, especially on a molar equivalent basis. Steady state exposures for the final dosing interval on Day 14 were similar to total compound exposure from single-dose PK. No clinical or histopathologic changes were observed after 14 days of exposure to Compounds 1, 2, or 5. Both clinical and histopathologic changes in the liver, including hepatocyte necrosis, was observed for animals administered VZHE-039 for 14 days.

TABLE 6

Summary of repeat-dose pharmacokinetic properties in rats

| Compound ID | $C_{max}$ (ng/ml) [μM] (male/female) | AUC0-∞ (ng · h/mL) [μM * h] (male/female) |
| --- | --- | --- |
| Voxelotor | 142,253 [422]/ 184,744 [548] | 2,279,147 [6,760]/ 2,567,945 [7,617] |
| VZHE-039 | 195,148 [753]/ 231,673 [894] | 3,003,535 [11,585]/ 3,159,917 [12,188] |
| Comp 1 | 161,057 [703]/ 122,473 [534] | 2,404,624 [10,490]/ 1,853,321 [8,085] |
| Comp 2 | 253,715 [1,107]/ 254,382 [1,110] | 4,668,020 [20,363]/ 4,939,391 [21,547] |
| Comp 5 | 211,029 [854]/ 245,508 [993] | 4,221,059 [17,073]/ 5,084,546 [20,566] |

Repeat oral doses administered at 100 mg/kg for 14 days

Experimental Section

Detailed Synthetic Methods

Synthesis of 2-hydroxy-6-(pyridin-3-ylmethoxy)benzaldehyde (Comp 1)

To a stirring solution of 2,6-dihydroxybezaldehyde (36.2 mmol) and potassium carbonate (36.2 mmol) in 3-pentanone, 3-bromomethylpyridine HBr (36.2 mmol) was added. The reaction was refluxed for 3 hours, and after completion, the solid precipitate was filtered and washed with 3-pentanone. The crude solid was purified by flash chromatography (1:1 hexane/ethyl acetate) to yield 1.62 g (19.5%) of light yellow granular solid. Mp 99-103 $^1$H NMR (80 MHz, CDCl$_3$) δ 11.93 (br s, 1H), 10.31 (s, 1H), 8.64 (dt, 2H, J=1.7, 4.4 Hz), 7.7-7.9 (m, 1H), 7.2-7.5 (m, 2H), 6.49 (dd, 2H, J=5.2, 8.4 Hz), 5.13 (s, 2H). 13C NMR (20 MHZ, CDCl$_3$) δ 193.9, 163.6, 161.1, 149.8, 148.9, 138.4, 135.3, 131.5, 123.7, 110.9, 110.5, 102.1, 68.1.

Synthesis of 2-hydroxy-6-(pyridin-2-ylmethoxy)benzaldehyde (Comp 2)

2-bromomethylpyridine HBr (60.966 mmol) followed by 2,6-dihydroxybenzaldehyde (1 eq), K$_2$CO$_3$ (3 eq), and dry acetone were added into a dry conical flask with a magnetic stirrer and flushed with N$_2$ gas. After sealing with a rubber stopper, N$_2$ was bubbled into the reaction mixture using a long needle. The mixture was stirred for 1 hour at room temperature, and then for another 1 hour at 60° C. with a small-gauge needle attached. After confirming completion of the reaction by TLC, the mixture was vacuum filtered through a bed of silica while hot, and washed with hot acetone. After evaporation, the crude material was purified by column chromatography using a 2:1 Hex/EtOAc system to yield 6.58 g (47%) of pale-yellow solid with the following characterization profile. Purity 99%. Mp=127.5-129.2° C. 1H NMR (80 MHz, CDCl$_3$) δ 12.03 (s, 1H), 10.54 (s, 1H), 8.67 (d. J=4.9 Hz, 1H), 7.81 (t, J=7.5 Hz, 1H), 7.44 (dd, J=10.2, 6.6 Hz, 3H), 6.55 (t, J=8.5 Hz, 2H), 5.34 (s, 2H).

Synthesis of 2-hydroxy-6-(pyridin-4-ylmethoxy)benzaldehyde (Comp 3)

A mixture of 2,6-dihydroxybenzaldehyde (1 eq), K$_2$CO$_3$ (3 eq), KI (0.1 eq), EtOAc (2 mL), and DMF (2 mL) in 50 mL 3-pentanone was sonicated for 5-10 minutes. 4-(Chloromethyl)pyridine HCl was then added, and sonicated at 60° C. for 90 minutes. The reaction mixture was transferred to a hot plate and stirred at 75° C. until reaction completion was confirmed by TLC. The mixture was vacuum filtered while hot, and washed with hot acetone. The filtrate was evaporated, and then purified by flash chromatography (Biotage Selekt, Safar HC 25 g) to give 0.252 g (11%) of pale yellow solid with the following characterization profile: Purity: 97%; melting point 140.8° C.; 1H NMR (80 MHZ,) δ 12.00 (s, 1H), 10.51 (s, 1H), 8.70 (s, 2H), 7.59-7.25 (m, 4H), 6.62 (d, J=8.5 Hz, 1H), 6.40 (d, J=7.4 Hz, 1H), 5.22 (s, 2H).

General Synthetic Procedure for Comps 4-8

To a solution of a substituted pyridine in dry acetone, 2,6-dihydroxybenzaldehyde (1 eq), K$_2$CO$_3$ (2 or 3 eq) and KI (0.1 eq) were added. After bubbling N$_2$ into the solution, the reaction mixture was stirred for 1 hour at room temperature, and then at 60° C. with a small-gauge needle attached. After confirming completion of the reaction by TLC, the mixture was vacuum filtered through a bed of silica while hot and washed with hot acetone. After evaporation, the crude was purified by column chromatography.

Synthesis of 2-((5-fluoropyridin-3-yl)methoxy)-6-hydroxybenzaldehyde (Comp 4)

3-(Chloromethyl)-5-fluoropyridine HCl (10 mmol) was reacted with 2,6-dihydroxybenzaldehyde according to the above general procedure. Purification of the crude material produced 0.942 g (38.1%) of pale-yellow solid with the following characterization profile: Purity: 97%; melting point 128-129° C.; 1H NMR (80 MHZ, CDCl$_3$) δ 11.92 (s, 1H), 10.35 (s, 1H), 8.46 (d, J=2.6 Hz, 2H), 7.57-7.18 (m, 3H), 6.47 (dd, J=13.6, 8.3 Hz, 2H), 5.15 (s, 2H).

Synthesis of 2-((3-fluoropyridin-2-yl)methoxy)-6-hydroxybenzaldehyde (Comp 5)

2-(Chloromethyl)-3-fluoropyridine HCl (17.141 mmol) was reacted with 2,6-dihydroxybenzaldehyde according to the above general procedure. Purification and crystallization from TBME produced 1.8 g (42.5%) of pale-yellow solid with the following characterization profile: Purity: 99%; melting point 132-136° C.; 1H NMR (80 MHZ, CDCl$_3$) δ 12.09 (s, OH), 10.48 (s, 1H), 8.57 (s, 1H), 7.54 (t, J=8.7 Hz, 3H), 6.93-6.29 (m, 2H), 5.46 (s, 2H).

Synthesis of 2-((2-fluoropyridin-3-yl)methoxy)-6-hydroxybenzaldehyde (Comp 6)

3-(Chloromethyl)-2-fluoropyridine (10 mmol) was reacted with 2,6-dihydroxybenzaldehyde according to the above general procedure. Purification of the crude material produced 0.924 g (37.4%) of pale-yellow solid with the following characterization profile: Purity: 97%; melting point 156-160° C.; 1H NMR (80 MHZ, CDCl$_3$) δ 11.97 (s, 1H), 10.42 (s, 1H), 8.41-7.65 (m, 2H), 7.64-7.04 (m, 3H), 6.76-6.33 (m, 2H), 5.23 (s, 2H).

Synthesis of 2-((2-chloropyridin-3-yl)methoxy)-6-hydroxybenzaldehyde (Comp 7)

2-Chloro-3-(chloromethyl)pyridine (10 mmol) was reacted with 2,6-dihydroxybenzaldehyde according to the above general procedure. Purification of the crude material produced 0.447 g (17%) of light beige solid with the following characterization profile: Purity: 97%; melting point 158-159° C.; 1H NMR (80 MHZ, CDCl$_3$) δ 11.98 (s, 1H), 10.38 (s, 1H), 8.52 (s, 1H), 7.69-7.16 (m, 3H), 6.58 (d, J=8.6 Hz, 2H), 5.36 (s, 2H).

Synthesis of 2-((3-chloropyridin-2-yl)methoxy)-6-hydroxybenzaldehyde (Comp 8)

3-Chloro-2-(chloromethyl)pyridine (10 mmol) was reacted with 2,6-dihydroxybenzaldehyde according to the above general procedure. Purification of the crude material produced 0.63 g (23.6%) of white solid with the following characterization profile: Purity: 99%; melting point 123-124° C.; $^1$H NMR (80 MHZ, CDCl$_3$) δ 11.84 (s, 1H), 10.26 (s, 1H), 8.39 (s, 1H), 7.65 (d. J=8.1 Hz, 1H), 7.43-6.93 (m, 3H), 6.42 (d, J=8.2 Hz, 2H), 5.26 (s, 2H).

Synthesis of 2,4-difluoro-6-(pyridin-2-ylmethoxy)benzaldehyde (Comp 9)

2-Bromomethylpyridine HBr (12.7 mmol) was reacted with 2,4-difluoro-6-hydroxybenzaldehyde according to the procedure for Comp 2. Purification of the crude material using a 1:3 Hex/CHCl$_3$ system, followed by crystallization from TBME produced pale-yellow solid material. Purity 99%. 1H NMR (80 MHZ, CDCl$_3$) δ 10.49 (s, 1H), 8.62 (s, 1H), 7.77 (d. J=11.1 Hz, 2H), 7.30 (d. J=4.8 Hz, 1H), 6.64 (d, J=8.9 Hz, 2H), 5.34 (s, 2H). $^{19}$F NMR (76 MHZ, CDCl$_3$) δ −94.41 (dd, J=23.4, 12.4 Hz), −108.93 (d, J=12.0 Hz).

General Synthetic Procedure for Comps 10-11

To a solution of a substituted pyrimidine in dry acetone, 2,6-dihydroxybenzaldehyde (1 eq), K$_2$CO$_3$ (3 eq), and KI (0.1 eq) were added. N$_2$ was bubbled into the solution, and the reaction mixture stirred at 60° C. with a small-gauge needle attached. After confirming reaction completion by TLC, the mixture was vacuum filtered while hot, and then washed with hot acetone. After evaporation, the crude was purified by column chromatography.

Synthesis of 2-hydroxy-6-(pyrimidin-5-ylmethoxy)benzaldehyde (Comp 10)

5-(Chloromethyl)pyrimidine HCl (6.06 mmol) was reacted with 2,6-dihydroxybenzaldehyde for 18 hours according to the above general procedure. Purification of the crude material using a 1:2:1 Hex/CHCl$_3$/EtOAc system, followed by crystallization from TBME produced 0.206 g (14.8%) of yellow solid with the following characterization profile: Purity: 99%; 1H NMR (80 MHz, CDCl$_3$) δ 11.91 (s, 1H), 10.31 (s, 1H), 9.21 (s, 1H), 8.81 (s, 2H), 7.61-7.07 (m, 1H), 6.49 (dd, J=11.3, 8.4 Hz, 2H), 5.13 (s, 2H).

Synthesis of 2-hydroxy-6-(pyrimidin-2-ylmethoxy)benzaldehyde (Comp 11)

2-(Chloromethyl)pyrimidine HCl HCl (6.06 mmol) was reacted with 2,6-dihydroxybenzaldehyde for 2 hours according to the above general procedure. Purification of the crude material using a 1:3 Hex/CHCl$_3$ system, followed by crystallization from TBME produced 0.423 g (15.7%) of yellow solid with the following characterization profile: Purity: 99%; 1H NMR (80 MHZ, CDCl$_3$) δ 12.02 (s, 1H), 10.55 (s, 1H), 8.82 (d, J=4.9 Hz, 2H), 7.53-7.09 (m, 2H), 6.50 (dd, J=11.4, 8.4 Hz, 2H), 5.42 (s, 2H).

Synthesis of 3-fluoro-2-hydroxy-6-(pyridin-3-ylmethoxy)benzaldehyde (Comp 12)

3-Bromomethylpyridine HBr (12.811 mmol) was reacted with 3-Fluoro-2,6-dihydroxybenzaldehyde according to the above procedure for Comp 2. Purification of the crude material using a 1:3 Hex/CHCl$_3$ system, followed by crystallization from TBME produced the product as pale-yellow solid. Purity 97%. 1H NMR (80 MHZ, CDCl$_3$) δ 11.40 (s, 1H), 10.16 (s, 1H), 8.59 (d. J=3.2 Hz, 2H), 7.73 (d, J=7.9 Hz, 1H), 7.43-6.99 (m, 2H), 6.75-6.38 (m, 1H), 5.30 (s, 2H).

Synthesis of 2,4-difluoro-6-((3-fluoropyridin-2-yl)methoxy)benzaldehyde (Comp 13)

A solution of 2,4-difluoro-6-hydroxybenzaldehyde (1 eq), K$_2$CO$_3$ (2 or 3 eq), and KI (0.1 eq) in dry acetone were heated at 40°C for 30 minutes. 2-(Chloromethyl)-3-fluoropyridine HCl (2.747 mmol) was warmed in dry acetone, and then added drop-wise to the aldehyde solution. The mixture was heated to 65° C. for 2 hours. After confirming reaction completion by TLC, the mixture was vacuum filtered while hot, and then washed with hot acetone. The filtrate was evaporated, and the crude purified by flash chromatography (Biotage Selekt, Safar HC 10 g column, 1:3 Hex/CHCl$_3$ isocratic system) to give 64 mg (8.7%) of off-white solid with the following characterization profile: Purity: 99%; 1H NMR (80 MHZ, CDCl$_3$) δ 10.39 (s, 1H), 8.52 (s, 1H), 7.75-7.15 (m, 3H), 7.00-6.27 (m, 2H), 5.43 (s, 2H).

Biochemical Assays.

Sickle Inhibition, Hb Adduct, and Hb Oxygen Equilibrium in SS Blood Suspensions.

All compounds (Comp 1-13) and comparator molecules (VZHE-039, PP-14, INN-310, and Voxelotor) were evaluated following established procedures. Blood samples from individual donors with homozygous SCD (obtained with informed consent) were diluted using Hemox buffer solution with the addition of glucose (10 mM) and BSA (0.2%) to adjust hematocrit of the blood suspensions to 20%, which standardizes the procedure to normalize the ratio of RBCs to drug, for assay consistency and reproducibility. Briefly, blood suspensions were incubated under room air in the presence of various concentrations of test compounds (0-2 mM) at 37° ° C. for 1 hour in 96-well round bottom plates. Subsequently, the suspensions were incubated with a hypoxic gas mixture (2.5% Oxygen gas/balance Nitrogen gas) at 37° C. for up to 2 hours prior to fixation with 2% glutaraldehyde solution without exposure to air. The fixated blood aliquots were evaluated by microscopic morphological analysis (image analysis on Image J software) to identify the proportion of sickled and non-sickled RBCs, and sickle inhibition calculated based on the % change from negative control (DMSO).

To establish oxygen-independent sickle inhibition, the incubation chamber was subsequently opened and exposed to room air for 15 minutes to ensure complete re-oxygenation and reversal of the sickled cells to normal round cells. Reversal was confirmed by microscopy. The incubation chamber was then closed, and the assay was repeated with incubation in 100% nitrogen gas for 1 hour (for screening), or up to 2.5 h (for time-course studies), with collection and fixation of blood aliquots at defined intervals. Aliquot samples were again subjected to microscopic morphological analysis of bright field images to identify the proportion of sickled and non-sickled cells, and sickle inhibition calculated.

The residual samples were then washed in phosphate-buffered saline, and hemolyzed in hypotonic lysis buffer, with or without sodium borohydride (50 mM). Aliquots obtained from the lysates with or without sodium borohydride (to reduce Schiff base adducts) were also assessed for level of Hb modification (drug-adduct formation) by cation-exchange HPLC (Hitachi D-7000 Series, Hitachi Instruments, Inc., San Jose, CA) with a weak cation-exchange column (Poly CAT A: 50 mm×4.6 mm, Poly LC, Inc., Columbia, MD). Hemoglobin isotype peaks are eluted with a linear gradient of phase B from 0% to 80% at A410 nm (Mobile Phase A: 40 mM Bis-Tris, 2 mM KCN, pH 6.9; Phase B: 40 mM Bis-Tris, 2 mM KCN, 0.2 M sodium chloride, pH 6.55). Clarified lysate from normal human adult Hb (Hb A), as well as commercial standards containing approximately equal amounts of Hb F. A. S and C (Helena Laboratories, Beaumont, TX), were utilized as reference isotypes. Reduced samples were used to assess "fixed adduct" formation (dependent on RBC membrane permeability), whereas non-reduced samples assessed drug-adduct formation independent of drug permeability.

Drug Partitioning Studies.

RBC partitioning studies were conducted both for SS RBCs following sickling studies above, or as separate independent studies with non-sickle blood. Briefly, aliquots of blood samples, which had been incubated with test molecules, were lysed either in deionized water (un-fixed), or in water containing 50 mM sodium borohydride (fixed).

Samples were subjected to cation exchange HPLC analyses, as described above. Modified Hb (Hb adducts) was determined as a proportion of total Hb in each sample, and partitioning ratio was determined as the relative fraction of Hb modification of fixed samples compared to corresponding non-fixed samples. The partitioning ratio is the relative fraction of Hb that was modified intracellularly by molecules that permeated the RBC membrane, as compared to unfixed adducts which reflect Hb binding without RBC membrane permeation.

Dose-Dependent P50 Shift in Human Blood.

Non-sickling human blood was incubated with test compounds at 0.25-2 mM concentrations at 37°C for 1 hour in 96-well round bottom plates. At conclusion, RBCs were washed once with PBS, followed by lysis with deionized water. Approximately 100 µl aliquots of individual lysates were added to 3 mL of 0.1M potassium phosphate buffer, pH 7.0 in a cuvette and subjected to hemoximetry analysis using a Hemox™ Analyzer (TCS Scientific Corp.) as previously described. Change in p50 values (Δp50) was calculated by subtracting the p50 values of treated samples from the value of the control sample and expressing the difference as a percentage of control p50 values.

In Vivo Pharmacokinetics and Safety Studies

Single doses of each compound were administered as oral suspensions by gavage in 0.5% carboxy methylcellulose at 100 mg/kg. Whole blood levels were collected for at least 72 hours after dose administration. Bioanalyses were performed with liquid chromatography-tandem mass spectrometry (LS-MS).

Repeat doses of each compound were administered once daily as oral suspensions by gavage in 0.5% carboxy methylcellulose for 14 days at 100 mg/kg. Whole blood was collected at 7 time-points for up to 24 hours during the final dosing interval on Day 14. Clinical observations, body weights, and food consumption were recorded throughout the 14 day study. Clinical chemistry and hematologic parameters were assessed, and histopathology was performed on organs after 14 days of exposure to study drug.

X-Ray Crystallography

Co-crystals of liganded Hb with compounds 1, 2, 5, and 8 were obtained following published methods. Briefly, 40-50 mg/mL of Hb in a round bottom flask was vacuumed for ~1 hour to remove oxygen and form deoxygenated Hb. Subsequently, carbon monoxide was bubbled into the deoxygenated Hb to form CO-ligated Hb (COHb). COHb was then incubated with a 10-20 molar excess of compounds 1, 2, 5, or 8 for about 1 hour to form COHb-compound complexes. Sodium cyanoborohydride ($NaCNBH_4$) was added at a 10 molar excess to reduce the reversible Schiff base adduct to the corresponding irreversible alkylamine covalent bond. COHb-compound complex solutions were then crystalized with 10-20% PEG 6000, 100 mM HEPES buffer, pH 7.4 using the batch method. X-ray diffraction data was collected at 100 K using Rigaku MicroMax™ 007HF X-ray Generator, Eiger R 4M Detector and Oxford Cobra Cryo-system (The Woodlands, TX). The crystals were first cryoprotected with 80 µL mother liquor mixed with 62 µL of 50% PEG6000. The diffraction data was processed using CrysAlisPro software (Rigaku) and the CCP4 suite of programs. The crystal structure of the complex was solved by the molecular replacement method with the Phenix program, using the native R2-state crystal structure (PDB ID 1BBB) as a search model. The structure was refined using Phenix and COOT.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound having a formula

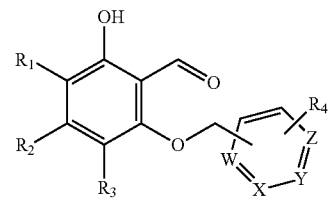

wherein
W, X, Y and Z are the same or different and are independently C or N, with the proviso that at least one of W, X, Y and Z is N; and
$R_1$, $R_2$, $R_3$, and Ra are the same or different and independently F, Cl or H, and pharmaceutically acceptable salts or oral prodrugs thereof.

2. The compound of claim 1 which is

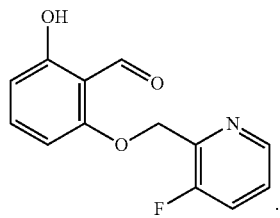 [SMILES: O=Cc1c(O)cccc1OCc1ncccc1F]

3. The compound of claim 1 which is

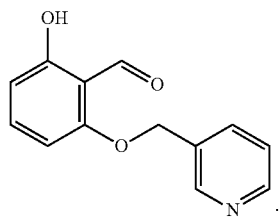

4. The compound of claim 1 which is

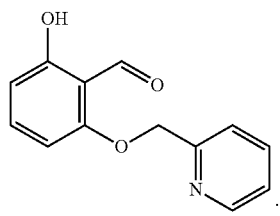

5. The compound of claim 1, wherein $R_1$, $R_2$, $R_3$, and $R_4$ are the same or different and least one is independently F or Cl.

6. The compound of claim 5, wherein the compound is

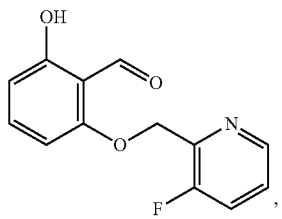

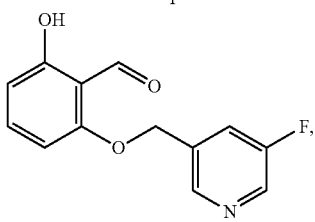

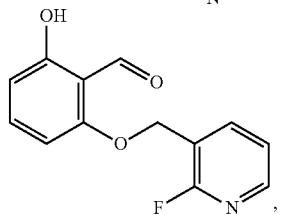

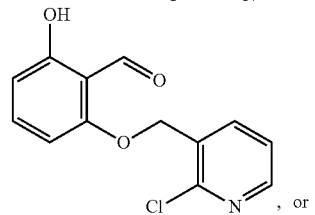

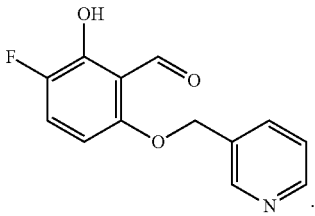

7. The compound of claim 1, wherein the compound is

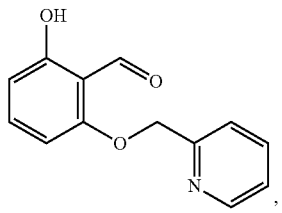 [SMILES: O=Cc1c(O)cccc1OCc1ccccn1]

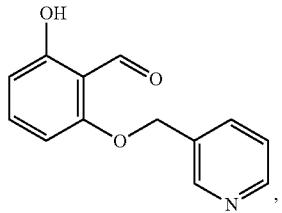

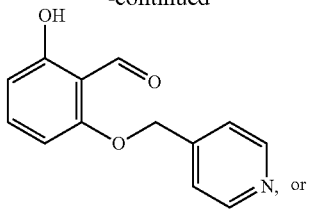

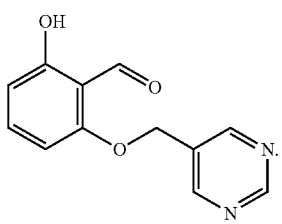

8. A method of preventing or treating one or more symptoms or conditions of sickle cell disease (SCD) in a subject in need thereof, comprising
administering to the subject a therapeutically effective amount of at least one compound of claim 1.

9. The method of claim 8, wherein the one or more symptoms or conditions are selected from the group consisting of red blood cell (RBC) sickling, adhesion of RBCs to tissue endothelium, oxidative stress and/or damage, hemolysis of RBCs, inflammation, vaso-occlusion, impaired microvascular blood flow, stroke, pain, and death.

10. The method of claim 8, wherein the step of administering is performed orally.

11. A method of preventing or treating one or more symptoms or conditions of sickle cell disease (SCD) in a subject in need thereof, comprising
administering to the subject a therapeutically effective amount of a compound, or a salt or prodrug which is metabolized or otherwise converted in a subject to said compound, having the formula

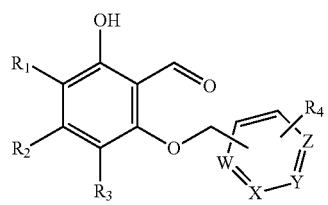

wherein
W, X, Y and Z are the same or different and are independently C or N, with the proviso that at least one of W, X, Y and Z is N; and
$R_1$, $R_2$, $R_3$, and Ra are the same or different and independently P, Cl or H.

* * * * *